US012079986B2

(12) United States Patent
Aoyama

(10) Patent No.: US 12,079,986 B2
(45) Date of Patent: Sep. 3, 2024

(54) MEDICAL IMAGE PROCESSING APPARATUS, SYSTEM, AND METHOD

(71) Applicant: CANON MEDICAL SYSTEMS CORPORATION, Otawara (JP)

(72) Inventor: Gakuto Aoyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 508 days.

(21) Appl. No.: 17/386,205

(22) Filed: Jul. 27, 2021

(65) Prior Publication Data

US 2022/0028069 A1    Jan. 27, 2022

(30) Foreign Application Priority Data

Jul. 27, 2020  (JP) .................................. 2020-126532
Jul. 26, 2021  (JP) .................................. 2021-121663

(51) Int. Cl.
*G06T 7/00*       (2017.01)
*G16H 15/00*    (2018.01)
*G16H 50/20*    (2018.01)

(52) U.S. Cl.
CPC ........... *G06T 7/0012* (2013.01); *G16H 15/00* (2018.01); *G16H 50/20* (2018.01); *G06T 2207/30096* (2013.01); *G06T 2207/30101* (2013.01)

(58) Field of Classification Search
CPC ......... G06T 7/0012; G06T 2207/30096; G06T 2207/30101; G16H 15/00; G16H 50/20
USPC ....................................................... 382/128
See application file for complete search history.

(56) References Cited

U.S. PATENT DOCUMENTS

| 2015/0051884 A1 | 2/2015 | Grady et al. |
| 2015/0051885 A1 | 2/2015 | Grady et al. |
| 2015/0051886 A1* | 2/2015 | Grady ................. A61B 5/0205 703/2 |
| 2015/0265222 A1* | 9/2015 | Sakaguchi ............. A61B 6/037 600/407 |
| 2016/0038251 A1 | 2/2016 | Grady et al. |
| 2016/0058407 A1* | 3/2016 | Wakai ..................... A61B 5/055 600/407 |
| 2016/0335766 A1* | 11/2016 | Ambwani ................ G06T 7/11 |

(Continued)

FOREIGN PATENT DOCUMENTS

| JP | 2011-062358 A | 3/2011 |
| JP | 2016-533815 A | 11/2016 |
| JP | 2020-518362 A | 6/2020 |

*Primary Examiner* — William D Titcomb
(74) *Attorney, Agent, or Firm* — Oblon, McClelland, Maier & Neustadt, L.L.P.

(57) ABSTRACT

A medical image processing apparatus according to an embodiment includes processing circuitry and an input interface. The processing circuitry obtains the spatial distribution of the wall shear stress values at each position of blood vessels. Moreover, the processing circuitry displays, from an arbitrary angle, a display image formed by assigning the wall shear stress values to a three-dimensional image. The input interface receives an input operation for changing the angle. During the display of the display image formed by assigning the wall shear stress values to the three-dimensional image, the processing circuitry changes the display form of the display image between a rotational display in which the display image is displayed while changing the angle with time, and a nonrotational display in which the angle is not changed.

26 Claims, 10 Drawing Sheets

(56) References Cited

U.S. PATENT DOCUMENTS

| | | | |
|---|---|---|---|
| 2017/0245821 A1* | 8/2017 | Itu | G06F 18/2413 |
| 2019/0117179 A1* | 4/2019 | Goyal | A61B 6/463 |
| 2019/0216417 A1* | 7/2019 | Shaughnessy | A61B 6/5217 |
| 2019/0358065 A1 | 11/2019 | Grady et al. | |
| 2019/0370956 A1* | 12/2019 | Jackson | A61B 6/5288 |
| 2020/0126219 A1 | 4/2020 | Wang et al. | |
| 2022/0028069 A1* | 1/2022 | Aoyama | G06T 7/0012 |

\* cited by examiner

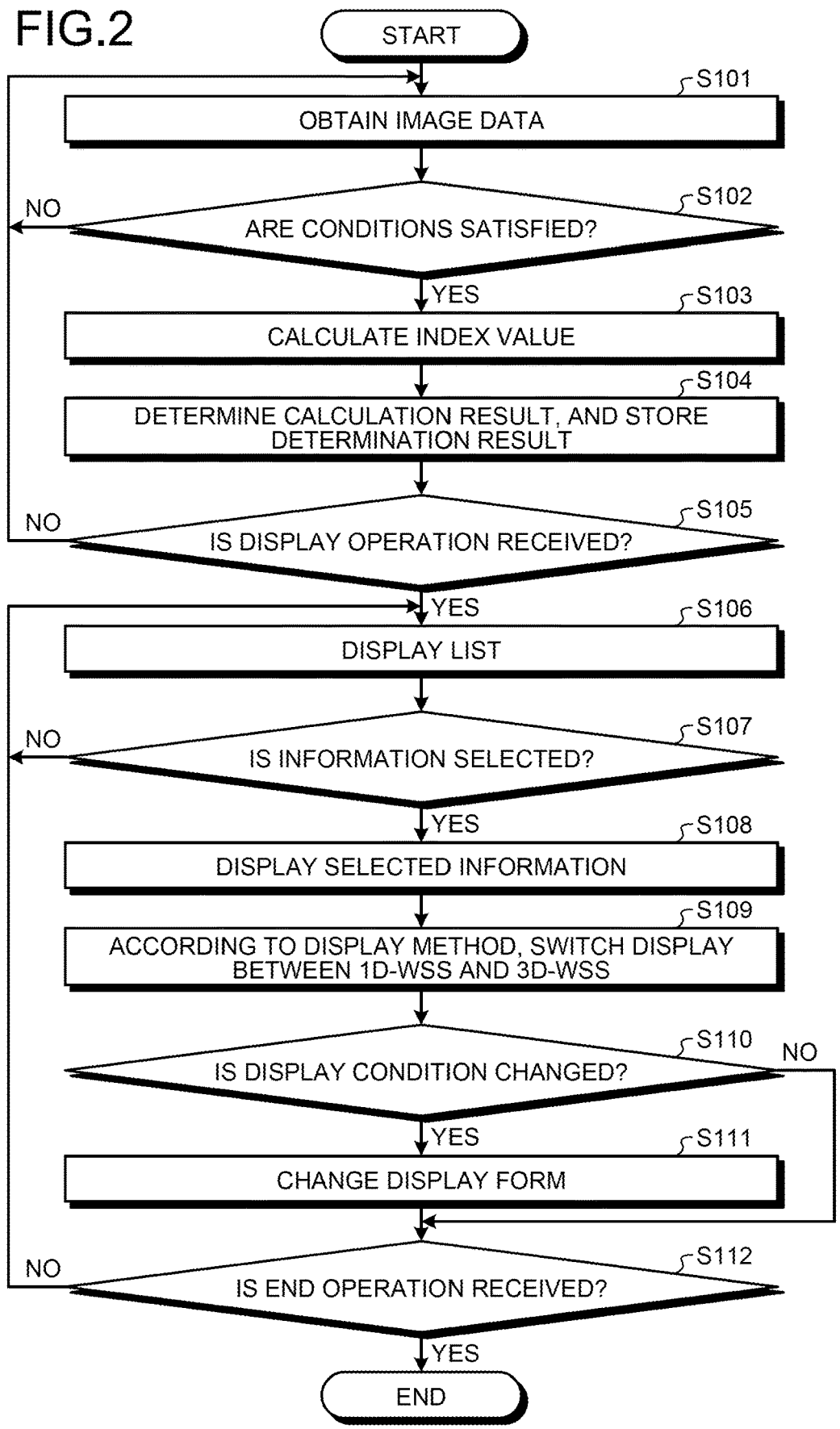

FIG.3A

| ID | PATIENT NAME | AVERAGE WSS | MAX WSS | MIN WSS | CALCIUM SCORE |
|---|---|---|---|---|---|
| 100000 | Aaa bbbb | 1 | 3 | 0.1 | 200 |
| 100001 | Aba hgis | 2 | 9 | 0.1 | 800 |
| 100002 | Acsd hour | 1 | 3 | 0.1 | 300 |

FIG.3B

| RCA | LAD | LCX |
|---|---|---|

| | AVERAGE WSS | MAX WSS | MIN WSS |
|---|---|---|---|
| SN | 1 | 3 | 0.2 |
| CB | 2 | 1 | 0.3 |
| RVB | 1 | 1 | 0.3 |
| AM | 0.4 | 9 | 0.1 |
| AVN | 1 | 2 | 0.6 |
| PD | 0.8 | 1 | 0.2 |

1D-WSS DISPLAY          3D-WSS DISPLAY

MEDICAL IMAGE PROCESSING APPARATUS, SYSTEM, AND METHOD

CROSS-REFERENCE TO RELATED APPLICATIONS

This application is based upon and claims the benefit of priority from Japanese Patent Application No. 2020-126532, filed on Jul. 27, 2020 and Japanese Patent Application No. 2021-121663, filed on Jul. 26, 2021; the entire contents of which are incorporated herein by reference.

FIELD

Embodiments described herein relate generally to a medical image processing apparatus, a system, and a method.

BACKGROUND

Conventionally, as a technology that supports performing diagnosis related to heart illnesses and supports formulating a treatment plan; a technology is known in which, based on the medical images related to the blood vessels of the heart of a subject, a variety of information regarding the blood flow in those blood vessels is presented. For example, a technology is known in which, as one of the types of information regarding the blood flow, the wall shear stress (WSS) at each position of the blood vessels is calculated and displayed.

BRIEF DESCRIPTION OF THE DRAWINGS

FIG. 2 is a flowchart for explaining the sequence of operations performed as a result of implementing the processing functions of processing circuitry of the medical image processing apparatus according to the first embodiment;

FIGS. 3A and 3B are diagrams illustrating an example of lists according to the first embodiment;

DETAILED DESCRIPTION

Exemplary embodiments of a medical image processing apparatus, a medical image processing system, and a medical image processing method are described below in detail with reference to the accompanying drawings. Meanwhile, the medical image processing apparatus, the medical image processing system and the medical image processing method according to the application concerned are not limited by the embodiments described below. Moreover, the embodiments can be combined with other embodiments and with the conventional technology without causing any contradictions in the operation details.

First Embodiment

Figure 1:
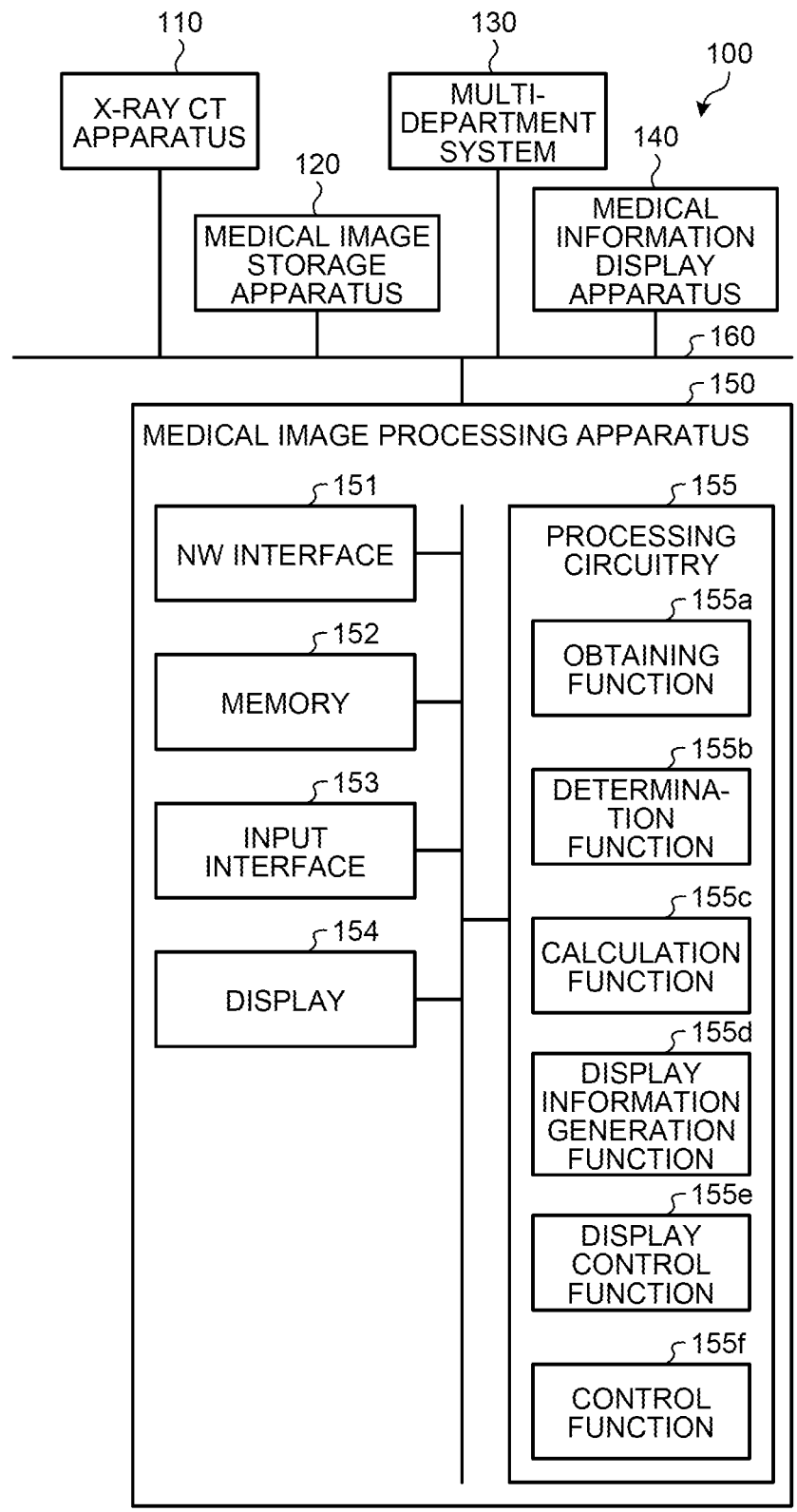
FIG. 1 is a diagram illustrating an exemplary configuration of a medical image processing system and a medical image processing apparatus according to a first embodiment.

FIG. 1 is a diagram illustrating an exemplary configuration of a medical image processing system and a medical image processing apparatus according to a first embodiment.

For example, as illustrated in FIG. 1, a medical image processing system 100 according to the first embodiment includes an X-ray CT apparatus 110 (CT stands for Computed Tomography), a medical image storage apparatus 120, a multi-department system 130, a medical information display apparatus 140, and a medical image processing apparatus 150. Herein, the apparatuses and the systems are communicably connected to each other via a network 160.

Moreover, apart from including the X-ray CT apparatus 110, the medical image processing system 100 can also include some other medical image diagnosis apparatus such as an MRI apparatus (MRI stands for Magnetic Resonance Imaging), an ultrasonic diagnosis apparatus, a PET apparatus (PET stands for Positron Emission Tomography), or a SPECT apparatus (SPECT stands for Single Photon Emission Computed Tomography).

The X-ray CT apparatus 110 generates CT images related to the subject. More particularly, in the X-ray CT apparatus 110, an X-ray tube and an X-ray detector are gyred in a circular orbit around the subject, and projection data is collected that represents the distribution of the X rays which have passed through the subject. Then, based on the collected projection data, the X-ray CT apparatus 110 generates CT images.

The medical image storage apparatus 120 archives various types of medical images related to the subject. More particularly, the medical image storage apparatus 120 obtains CT images from the X-ray CT apparatus 110 via the network 160, and stores them in an internal memory. The medical image storage apparatus 120 is implemented using, for example, a computer apparatus such as a server or a workstation. Alternatively, for example, the medical image storage apparatus 120 is implemented using the picture archiving and communication system (PACS), and archives CT images in a DICOM-compatible format (DICOM stands for Digital Imaging and Communications in Medicine).

The multi-department system 130 includes various systems such as a hospital information system (HIS), a radiology information system (RIS), a diagnosis report system, a laboratory information system (LIS), a rehabilitation department system, a dialysis department system, and a surgery department system. The medical image processing system 100 is connected to each of those systems, and communicates a variety of information with them. For example, the medical image processing system 100 communicates information such as subject information, examination information, treatment information, and analysis results with the systems included in the multi-department system 130.

The medical information display apparatus 140 displays a variety of medical information regarding the subject. More particularly, the medical information display apparatus 140 obtains medical information such as CT images and results of image processing from the medical image storage apparatus 120, and displays such medical information in a display installed therein. For example, the medical information display apparatus 140 is implemented using a computer apparatus such as a workstation, a personal computer, or a tablet terminal.

The medical image processing apparatus 150 performs a variety of image processing in regard to the subject. More particularly, the medical image processing apparatus 150 obtains CT images from the X-ray CT apparatus 110 or the medical image storage apparatus 120 via the network 160, and performs a variety of image processing using those CT images. Moreover, the medical image processing apparatus 150 obtains a variety of information from the multi-department system 130 via the network 160, and performs a variety of processing. The medical image processing apparatus 150 is implemented using, for example, a computer apparatus such as a server or a workstation.

For example, the medical image processing apparatus 150 includes a network (NW) interface 151, a memory 152, an input interface 153, a display 154, and processing circuitry 155.

The NW interface 151 controls the transmission of a variety of data and communication between the medical image processing apparatus 150 and other apparatuses connected via the network 160. More particularly, the NW interface 151 is connected to the processing circuitry 155; and outputs the data received from other apparatuses to the processing circuitry 155 or sends the data output from the processing circuitry 155 to other apparatuses. The NW interface 151 is implemented using, for example, a network card, a network adaptor, or a network interface controller (NIC).

The memory 152 is used to store a variety of data and various computer programs. More particularly, the memory 152 is connected to the processing circuitry 155; stores the data that is input from the processing circuitry 155; and reads the stored data and outputs it to the processing circuitry 155. For example, the memory 152 is implemented using a semiconductor memory device such as a random access memory (RAM) or a flash memory; or using a hard disk; or using an optical disk.

The input interface 153 receives input operations regarding various instructions and a variety of information from the user. More particularly, the input interface 153 is connected to the processing circuitry 155; and converts an input operation received from the user into an electrical signal and outputs it to the processing circuitry 155. The input interface 153 is implemented using, for example, one of the following: a trackball; switch buttons; a mouse; a keyboard; a touchpad for performing input operations by touching an operation screen; a touch-sensitive screen in which a display screen and a touchpad are integrated; a contactless input interface in which an optical sensor is used; or a voice interface. Meanwhile, in the present written description, the input interface 153 is not limited to a physical operating component such as a mouse or a keyboard. Alternatively, as an example as the input interface 153, it is possible to use an electrical signal processing circuit that receives an electrical signal corresponding to an input operation from an external input device installed in a separate device, and then outputs the electrical signal to a control circuit.

For example, the input interface 153 receives an input operation for changing the angle of the display image that is being displayed from an arbitrary angle. Meanwhile, the input interface 153 represents an example of an input operation receiving unit.

The display 154 displays a variety of information and a variety of data. More particularly, the display 154 is connected to the processing circuitry 155, and displays a variety of information and a variety of data output from the processing circuitry 155. For example, the display 154 is implemented using a liquid display, a cathode ray tube (CRT) display, or a touch-sensitive panel.

The processing circuitry 155 controls the medical image processing apparatus 150 in entirety. For example, the processing circuitry 155 performs a variety of processing according the input operations received from the user via the input interface 153. For example, the processing circuitry 155 receives input of data, which is sent from another apparatus, from the NW interface 151; and stores the input data in the memory 152. Moreover, for example, the processing circuitry 155 outputs the data stored in the memory 152 to the NW interface 151, so that the data is sent to another apparatus. Furthermore, for example, the processing circuitry 155 displays the data, which is stored in the memory 152, in the display 154.

Till now, the explanation was given about an exemplary configuration of the medical image processing system 100 and the medical image processing apparatus 150 according to the first embodiment. For example, the medical image processing system 100 and the medical image processing apparatus 150 according to the first embodiment are installed in a medical facility such as a hospital or a health clinic, and support the user such as a doctor to perform diagnosis related to heart illnesses and to formulate a treatment plan.

More particularly, based on the medical information regarding the blood vessels of the heart of a subject, the medical image processing apparatus 150 calculates and displays the wall shear stress (WSS) at each position of the blood vessels. Herein, by taking into account the WSS calculation cost and the visibility for the doctor, the medical image processing apparatus 150 automatically changes the display form, so as to reduce the time and efforts required by the user to perform diagnosis related to heart illnesses and to formulate a treatment plan.

Regarding the WSS, the calculation cost and the accuracy differs according to the calculation method. Hence, if the control is not appropriately performed by taking into account the objective of the user, there is a possibility of involving unnecessary calculation cost or a possibility of not being able to calculate the WSS to the accuracy demanded by the user. On the other hand, in order to manually set the calculation method by taking into account various situations, it requires time and efforts of the user.

In that regard, the medical image processing apparatus 150 according to the first embodiment is configured to appropriately control the calculation and the display of the WSS by taking into account the objective of the user, thereby enabling achieving reduction in the time and efforts required by the user.

More particularly, according to the different WSS display methods, the medical image processing apparatus 150 changes the display form of the WSS. For example, at the time of displaying a three-dimensional image of the blood vessels in which the WSS is indicated, the medical image processing apparatus 150 changes the display form depending on whether the rotational display or the nonrotational display is to be performed. Given below is the detailed explanation about the medical image processing apparatus 150 having the configuration explained above. The following explanation is given for an example in which coronary CT images are used as the medical images related to the blood vessels.

For example, as illustrated in FIG. 1, in the first embodiment, the processing circuitry 155 of the medical image processing apparatus 150 implements an obtaining function 155a, a determination function 155b, a calculation function 155c, a display information generation function 155d, a display control function 155e, and a control function 155f. The obtaining function 155a represents an example of an obtaining unit. The determination function 155b represents an example of a determining unit. The calculation function 155c represents an example of a calculating unit. The display information generation function 155d represents an example of a generating unit. The display control function 155e represents an example of a display control unit. The control function 155f represents an example of a control unit.

The obtaining function 155a obtains coronary CT images of the subject from the X-ray CT apparatus 110 or the medical image storage apparatus 120 via the NW interface 151. More particularly, the obtaining function 155a obtains three-dimensional coronary CT images that can be used in calculating the WSS. Moreover, the obtaining function 155a can obtain, via the NW interface 151, index values related to the blood flow from an apparatus connected to the medical image processing system 100. That is, the obtaining function 155a can obtain index values related to the blood flow that are calculated by an apparatus connected to the medical image processing system 100. For example, the obtaining function 155a obtains the WSS value at each position of the coronary artery as calculated by an apparatus connected to the medical image processing system 100, and obtains the fractional flow reserve (FFR). Meanwhile, in the first embodiment, the explanation is given for the case in which the calculation function 155c calculates the index values related to the blood flow using a three-dimensional coronary CT image obtained by the obtaining function 155a.

The determination function 155b performs determination related to the WSS calculation target and the WSS calculation result. More particularly, the determination function 155b performs a determination operation regarding the validness of the WSS calculation target and performs a determination operation regarding the validness of the WSS calculation result. Regarding the operations performed by the determination function 155b, the detailed explanation is given later.

The calculation function 155c extracts the center line of the coronary artery captured in the coronary CT image of the subject as obtained by the obtaining function 155a. Moreover, based on the coronary CT image of the subject that is obtained by the obtaining function 155a, the calculation function 155c calculates the index values related to the blood flow of the coronary artery. For example, according to a known method in which computational fluid dynamics (CFD) or machine learning is used, from the coronary CT image of the subject, the calculation function 155b calculates the WSS value at each position of the coronary artery and calculates the fractional flow reserve (FFR).

For example, in the case of calculating the index values according to the CFD, the calculation function 155c performs fluid analysis using the following: the physical property value of the blood (for example, hematocrit, blood viscosity, or blood density); the value of elasticity of the vascular wall; the conditions for iterative calculation (the maximum iterative count, the relaxation coefficient, and the permissible value of the residual error); and the analysis conditions such as the initial values of analysis (the initial values of the blood flow volume, the pressure, the fluid resistance, and the pressure boundary); and calculates the index values related to the blood flow in the target region of the blood vessels. As an example, the calculation function 155c calculates, for each position of the coronary artery, the index values such as the pressure, the blood flow volume, the flow velocity of the blood, the vector, and the wall shear stress.

The display information generation function 155d generates various display images and generates display information containing a variety of information. For example, the display information generation function 155d performs three-dimensional reconstruction of the vascular region of the coronary artery in a coronary CT image, and generates three-dimensional images of the coronary artery. As an example, the display information generation function 155d generates volume rendering (VR) images, surface rendering (SR) images, curved planar reconstruction (CPR) images, multi planar reconstruction (MPR) images, and stretched multi planar reconstruction (SPR) images.

Moreover, for example, the display information generation function 155d generates subject information and a variety of display information such as the calculation result obtained by the calculation function 155c. Regarding the display information generated by the display information generation function 155d, the detailed explanation is given later.

The display control function 155e displays the display information, which is generated by the display information generation function 155d, in the display 154; and controls the display state. More particularly, the display control function 155e performs control to display, from an arbitrary angle, a display image formed when WSS values are assigned to a three-dimensional image. For example, the display control function 155e controls the rotational display of the display image that indicates the WSS calculated by the calculation function 155c. Meanwhile, regarding the operations performed by the display control function 155e, the detailed explanation is given later.

The control function 155f sends the WSS calculation result to a predetermined destination, and performs various operations. Regarding the operations performed by the control function 155f, the detailed explanation is given later.

The processing circuitry 155 is implemented using, for example, a processor. In that case, the abovementioned processing functions are stored in the form of computer-executable programs in the memory 152. Then, the processing circuitry 155 reads the computer programs from the memory and executes them so as to implement the corresponding processing functions. In other words, as a result of reading the computer programs, the processing circuitry 155 gets equipped with the processing functions illustrated in FIG. 1.

Meanwhile, the processing circuitry 155 can be configured using a combination of a plurality of independent processors, and each processor can execute computer programs to implement the corresponding processing functions. The processing functions of the processing circuitry 155 can be dispersed or integrated among one or more processing circuits. Alternatively, the processing functions of the processing circuitry 155 can be implemented using a combination of hardware, such as a circuit, and software. Meanwhile, herein, although the explanation is given for the case in which the computer programs corresponding to the processing functions are stored in a single memory 152, the first embodiment is not limited by that case. Alternatively, for example, the configuration can be such that the computer programs corresponding to the processing functions are stored in a dispersed manner across a plurality of memories, and the processing circuitry 155 reads the computer programs from those memories and executes them.

As explained above, at the time of displaying a three-dimensional image of the blood vessels in which the WSS is indicated, the medical image processing apparatus 150 changes the display form depending on whether the rotational display or the nonrotational display is to be performed. In that regard, firstly, explained below with reference to FIG. 2 is the sequence of operations performed by the medical image processing apparatus 150. FIG. 2 is a flowchart for explaining the sequence of operations performed as a result of implementing the processing functions of the processing circuitry 155 of the medical image processing apparatus 150 according to the first embodiment. With reference to FIG. 2, the explanation is given for the case in which the WSS is calculated in advance even before receiving a WSS calculation instruction from the user.

For example, as illustrated in FIG. 2, in the first embodiment, the obtaining function 155a obtains a coronary CT image of the subject from the X-ray CT apparatus 110 or the medical image storage apparatus 120 (Step S101). For example, every time the X-ray CT apparatus 110 collects a coronary CT image or every time a coronary CT image is stored in the medical image storage apparatus 120, the obtaining function 155a obtains that coronary CT image. This operation is implemented when, for example, the processing circuitry 155 calls the computer program corresponding to the obtaining function 155a from the memory 152 and executes it.

Then, the determination function 155b determines whether or not the conditions are satisfied if the obtained coronary CT image is treated as the target (Step S102). More particularly, the determination function 155b determines whether or not the obtained coronary CT image has validness as the target for WSS calculation. This operation is implemented when, for example, the processing circuitry 155 calls the computer program corresponding to the determination function 155b from the memory 152 and executes it.

If the determination function 155b determines that the conditions are satisfied (Yes at Step S102), then the system control proceeds to Step S103. On the other hand, if the determination function 155b determines that the conditions are not satisfied (No at Step S102), then the system control returns to Step S101; and the medical image processing apparatus 150 obtains image data.

Subsequently, based on the coronary CT image of the subject as obtained by the obtaining function 155a, the calculation function 155c calculates an index value related to the blood flow (Step S103). For example, the calculation function 155c calculates the WSS. This operation is implemented when, for example, the processing circuitry 155 calls the computer program corresponding to the calculation function 155c from the memory 152 and executes it.

Then, the determination function 155b performs determination of the calculation result, and stores the determination result in the memory 152 (Step S104). More particularly, the determination function 155b determines whether or not the WSS calculation result obtained by the calculation function 155c has validness. Subsequently, the determination function 155b stores the determination result in the memory 152 in a corresponding manner to identification information that enables identification of the subject. This operation is implemented when, for example, the processing circuitry 155 calls the computer program corresponding to the determination function 155b from the memory 152 and executes it.

Subsequently, the display control function 155e determines whether or not a display operation for displaying the index value is received via the input interface 153 (Step S105). If the display control function 155e has received a display operation (Yes at Step S105), then the system control proceeds to Step S106. On the other hand, if the display control function 155e has not received a display operation (No at Step S105), then the system control returns to Step S101; and the medical image processing apparatus 150 obtains image data. This operation is implemented when, for example, the processing circuitry 155 calls the computer program corresponding to the display control function 155e from the memory 152 and executes it.

Then, the display information generation function 155d generates a list indicating the index value for each subject, and the display control function 155e displays the generated list in the display 154 (Step S106). This operation is implemented when, for example, the processing circuitry 155 calls the computer programs corresponding to the display information generation function 155d and the display control function 155e from the memory 152 and executes them.

Subsequently, the display control function 155e determines whether or not a selection operation with respect to the list is received via the input interface 153 (Step S107). If the display control function 155e has received the selection operation (Yes at Step S107), then the system control proceeds to Step S108. On the other hand, if the display control function 155e has not received the selection operation (No at Step S107), then the medical image processing apparatus 150 keeps on displaying the list. This operation is implemented when, for example, the processing circuitry 155 calls the computer program corresponding to the display control function 155e from the memory 152 and executes it.

Then, the display information generation function 155d generates display information regarding the selected information, and the display control function 155e displays the generated display information in the display 154 (Step S108). This operation is implemented when, for example, the processing circuitry 155 calls the computer programs corresponding to the display information generation function 155d and the display control function 155e from the memory 152 and executes them.

Subsequently, according to the display method, the display control function 155e switches the display between a display image (1D-WSS) in which the spatial distribution of the WSS value at each cross-sectional position of the blood vessels with reference to the center line of the blood vessels is indicated in an image of the coronary artery, and a display image (3D-WSS) in which the spatial distribution of the WSS value at each position in the blood vessels or the vascular walls is indicated in an image of the coronary artery (Step S109). For example, the display control function 155e changes the display form in such a way that the 1D-WSS is displayed during the rotational display in which the display image is displayed while varying the angle with time, and that the 3D-WSS is displayed during the nonrotational display in which the angle is not varied. As an example, when the input interface 153 receives an operation for varying the display angle of the display image, the display control function 155e displays the 1D-WSS. On the other hand, when an operation for varying the display angle is not received, the display control function 155e displays the 3D-WSS. This operation is implemented when, for example, the processing circuitry 155 calls the computer program corresponding to the display control function 155e from the memory 152 and executes it.

Then, the display control function 155e determines whether or not the display condition is changed (Step S110). For example, the display control function 155e determines whether or not the rotation condition or the display condition is changed. As an example, the display control function 155e determines whether or not the rotation condition including at least either the rotation count or the rotation speed is changed, or whether or not the display condition including magnification or reduction is changed. If the display condition is changed (Yes at Step S110), then the display control function 155e further changes the display form (Step S111).

As an example, when the 1D-WSS is being displayed during the rotational display; if the rotation speed of the display image is reduced, the display control function 155e changes the display image from the 1D-WSS to the 3D-WSS. Moreover, for example, when the 1D-WSS is being displayed during the rotational display; if the display image is magnified, the display control function 155e changes the type of the image for displaying the WSS. On the other hand, if the display condition is not changed (No at Step S110), then the system control proceeds to Step S112. This operation is implemented when, for example, the processing circuitry 155 calls the computer program corresponding to the display control function 155e from the memory 152 and executes it.

Subsequently, the display control function 155e determines whether or not an end operation is received via the input interface 153 (Step S112). If an end operation is received (Yes at Step S112), then the medical image processing apparatus 150 ends the operations. On the other hand, if an end operation is not received (No at Step S112), then the system control returns to Step S106 and the medical image processing apparatus 150 again displays the list.

Given below is the detailed explanation of the operations performed by the medical image processing apparatus 150.

Determination Operation Related to Calculation Target

As explained with reference to Step S102 illustrated in FIG. 2, in the WSS calculation, the determination function 155b determines the validness of the calculation target. More particularly, the determination function 155b determines the validness of the calculation target using preset conditions.

For example, regarding the coronary CT image obtained at Step S101, the determination function 155b determines whether or not the WSS can be calculated. As an example, regarding a coronary CT image, the determination function 155b determines whether or not the following four conditions are satisfied: "1: the heart is present within the imaging range", "2: contrast radiography is performed", "3: electrocardiographic synchronous imaging is performed", and "4: the heart rate is collected at 70 or less".

In that case, for example, the determination function 155b can obtain the information about the abovementioned four conditions from the DICOM header of the coronary CT image, and perform the determination operation. Alternatively, the determination function 155b can communicate with the multi-department system 130 to obtain the information about the abovementioned four conditions, and perform the determination operation.

Meanwhile, the determination function 155b can perform determination using an image processing technology too. For example, the determination function 155b can implement an image processing technology to search an image for the anatomical structure of the heart; and, if the concerned anatomical structure cannot be detected, can determine that the condition "1: the heart is present within the imaging range" is not satisfied. Moreover, if the anatomical structure of the coronary artery cannot be detected from the image according to an image processing technology or if the pixel values at the position of the coronary artery are small, then the determination function 155b can determine that the condition "2: contrast radiography is performed" is not satisfied.

Meanwhile, the conditions for the determination of whether or not the WSS can be calculated are not limited to the four conditions mentioned above, and various other conditions can be used.

For example, in order to determine whether or not the WSS can be calculated, the determination function 155b can determine whether or not the protocol of the obtained coronary CT image is included in the range of the recommended protocol that is meant for collecting the coronary CT images to be used in the calculation of the index values related to the blood flow. As an example, the determination function 155b determines whether or not the slice thickness or the matrix size in the obtained CT image is within the range of the recommended protocol.

Moreover, for example, in order to determine whether or not the WSS can be calculated, the determination function 155b detects the movement of the subject at the time of taking images or detects the noise in the images that is attributed to a metal (a stent or a pacemaker), and determines whether or not the amount of noise has exceeded a threshold value. As an example, the determination function 155b calculates the signal-to-noise (S/N) ratio in the obtained coronary CT image; compares the S/N ration with a threshold value; and determines whether or not the WSS can be calculated from the obtained coronary CT image.

Furthermore, for example, the determination function 155b can perform the determination operation by combining a plurality of conditions. For example, conditions are set with respect to the inconsistency between the date of examination and the date of imaging or with respect to the validness in the subject information. As an example, if an obtained coronary CT image has the date of examination as "year 2020" and has the date of imaging as "year 2019", then the determination function 155b determines that the WSS calculation is not possible using that coronary CT image. Alternatively, for example, if the age indicates "30 years old" but the body weight indicates "10 kg", then the determination function 155b determines that the information regarding the subject has low validness and determines that the WSS calculation is not possible.

Moreover, for example, the determination function 155b can perform the determination operation also using the information regarding the medication profile of the subject. As an example, the determination function 155b obtains the information regarding the medication profile of the subject from the multi-department system 130; and, if aspirin or a vasodilator was administered immediately before the imaging, determines that the WSS calculation is not possible due to the fact that a different calculation result than the normal result is likely to be calculated.

Operation for Calculating Index Value

As explained earlier with reference to Step S103 illustrated in FIG. 2, the calculation function 155c calculates an index value related to the blood flow. More particularly, the calculation function 155c calculates the WSS value at each position of the coronary artery.

For example, as explained above, the calculation function 155c implements a known method such as CFD or machine learning and calculates the WSS values in the obtained coronary CT image. Meanwhile, the calculation function 155c can calculate the one-dimensional WSS (hereinafter, referred to as 1D-WSS) and the three-dimensional WSS (hereinafter, referred to as 3D-WSS). More particularly, the calculation function 155c calculates the 1D-WSS indicating the WSS at each cross-sectional position of the blood vessels with reference to the center line of the blood vessels, and calculates the 3D-WSS indicating the WSS at each position in the blood vessels or the vascular walls.

Meanwhile, regarding any other index value related to the blood flow other than the WSS, the calculation function 155c can calculate one-dimensional values and three-dimensional values. For example, the calculation function 155c can calculate 1D-FFR indicating the FFR at each cross-sectional position of the blood vessels with reference to the center line of the blood vessels, and can calculate 3D-FFR indicating the FFR at each position in the blood vessels.

In the 3D-FFR or the 3D-WSS, since the WSS or the FFR is calculated for the local positions, the advantage is that more accurate information can be provided. However, at the same time, there is a disadvantage that the calculation time and the calculation cost, such as the processing by a computer and the usage of a memory area, is high. As compared to the 3D-FFR or the 3D-WSS, the 1D-FFR or the 1D-WSS has the disadvantage that the accuracy of the information undergoes a decline. However, the advantage is that the calculation time and the calculation cost, such as the processing by a computer or the usage of a memory area, is low.

Meanwhile, regarding the calculation of an index value by the calculation function 155c, the medical image processing apparatus 150 can receive the manual setting of CFD parameters via the input interface 153.

Determination Operation Related to Calculation Result

As explained above with reference to FIG. 2, the determination function 155b determines the validness of the WSS calculation result. More particularly, the determination function 155b determines the validness of the calculation result using preset conditions.

For example, in the WSS calculation attempted by the calculation function 155c, if the WSS calculation could not be performed due to some aberration in calculation or if the calculation result or the calculation process deviates from the preset standard, then the determination function 155b determines that the calculation result does not have validness. As an example, at each position of the coronary artery or for each branch vessel, the determination function 155b performs determination about the WSS calculation result; and stores the determination result in a corresponding manner to the position or the branch vessel.

In the determination of the calculation result, for example, a shape model of a standard coronary artery is used that is generated in advance using a large volume of image data, or a preset WSS reference value is used. As an example, the determination function 155b calculates the degree of deviation of the shape of the coronary artery calculated during the WSS calculation process with respect to the standard shape model of the coronary artery; and, if the calculated degree of deviation exceeds a threshold value, determines that the calculation result does not have validness. Moreover, for example, the determination function 155b calculates the degree of deviation of the calculated WSS values with respect to the reference value; and, if the calculated degree of deviation exceeds a threshold value, determines that the calculation result does not have validness.

Meanwhile, the determination function 155b can perform the determination using the calculated body of fluid. In that case, if the fluid distribution indicates backflow of blood over a wide range of blood vessels, which is an inconceivable phenomenon in a normal subject; then the determination function 155b determines that the calculation result does not have validness.

In the case of the WSS, the stress normally occurs along the directions based on the direction of travel of the blood vessels. In that regard, in the WSS calculation result, if points having the stress in the inward-outward direction of the blood vessels are generated over a region having a predetermined size or more, then the determination function 155b can determine that the calculation result does not have validness.

Moreover, if there is inconsistency in the parameters that are manually set via the input interface 153 (for example, for the image size of 100*100, the mesh size of 50*50 and the mesh count of 100 is set) or if the manually-set parameters do not have validness (for example, if the parameters are off the range of the recommended protocol), then the determination function 155b can determine that the calculation result does not have validness.

List Display Operation

As explained earlier with reference to FIG. 2, when a display operation is received from the user, the display control function 155e firstly displays a list indicating the WSS calculation result for each subject. More particularly, the display information generation function 155d makes use of various calculation results obtained by the calculation function 155c and makes use of subject information, and generates a list indicating the WSS calculation result for each subject. Then, the display control function 155e displays the list, which is generated by the display information generating function 155d, in the display 154. FIGS. 3A and 3B are diagrams illustrating an example of the lists according to the first embodiment.

For example, when a display operation is received from the user, the display control function 155e displays, in the display 154, a list in which the following items are held in a corresponding manner: "ID", "Patient name", "Average WSS", "Max WSS", "Min WSS", and "Calcium Score". The item "ID" represents an identifier enabling unique identification of the subject. The item "Patient name" represents the name of the subject. The item "Average WSS" represents the average value of the calculated WSS values. The item "Max WSS" represents the maximum value among the calculated WSS values. The item "Min WSS" represents the minimum value among the calculated WSS values. The item "Calcium Score" represents the calcium score in the blood vessels for which the WSS is calculated.

Herein, the display control function 155e highlights such results in the list which are deviating from the reference value. More particularly, the display control function 155e compares a preset reference value with the values calculated by the calculation function 155c, and highlights the results having the degree of deviation equal to or greater than a threshold value. For example, as illustrated in FIG. 3A, the display control function 155e highlights the "Max WSS: 9" corresponding to the "ID: 100001".

Moreover, the display control function 155e can further display, in the list, the analysis results not related to the WSS. For example, as illustrated in FIG. 3A, the display control function 155e displays the calcium score that is not related to the WSS. Herein, in the list illustrated in FIG. 3A, only the calcium score is illustrated as the analysis result not related to the WSS. However, the first embodiment is not limited by that example. Alternatively, for example, the presence or absence of plaque or the FFR value can also be displayed in a corresponding manner.

Meanwhile, other than displaying the list illustrated in FIG. 3A, the display control function 155e can display various other types of lists. For example, when the "Max WSS: 9" corresponding to the "ID: 100001" is selected from the list illustrated in FIG. 3A, the display control function 155e changes the display information to display a list of WSS details in each branch vessel as illustrated in FIG. 3B.

The list illustrated in FIG. 3B indicates the items "Average WSS", "Max WSS", and "Min WSS" for each branch vessel in the "RCA", the "LAD", and the "LCX" of the coronary artery. For example, as illustrated in FIG. 3B, the display control function 155e displays tabs for the "RCA", the "LAD", and the "LCX"; and, regarding the branch vessel corresponding to the selected tab, displays a list of the items "Average WSS", "Max WSS", and "Min WSS". With reference to FIG. 3B, since the "Max WSS: 9" that is highlighted in FIG. 3A is selected, the "RCA" tab that includes the result "Max WSS: 9" is automatically selected; and a list is displayed in which the items "Average WSS", "Max WSS", and "Min WSS" are listed for the branch vessels "SN", "CB", "RVB", "AM", "AVN", and "PD" present in the "RCA".

Similarly, if the user selects the "LAD" tab or the "LCX" tab, then the display control function 155e displays a list in which the items "Average WSS", "Max WSS", and "Min WSS" are listed for the branch vessels included in the selected tab (the "LAD" tab or the "LCX" tab).

WSS Display Operation

As explained earlier with reference to Step S108, when a selection operation with respect to a list is received, the display control function 155e performs control to display the WSS for the selected subject (or the selected branch vessel). More particularly, firstly, the display information generation function 155d generates a three-dimensional image of the blood vessel for which the WSS value is calculated at each position. Then, the display control function 155e displays a display image formed when the WSS values are reflected in a three-dimensional image.

For example, the display information generation function 155d generates a VR image of the coronary artery of the selected subject. Then, the display control function 155e displays a color image formed when colors according to the WSS values are mapped in the VR image of the coronary artery. In that case, the display control function 155e obtains the WSS values at all positions of the coronary artery as calculated by the calculation function 155c, and identifies the available WSS range from the maximum WSS value and the minimum WSS value. Then, the display control function 155e sets an arrangement of colors (a color lookup table) with respect to the identified WSS range; and, at each position of the coronary artery, maps a color according to the WSS value for that position.

Figure 4A:
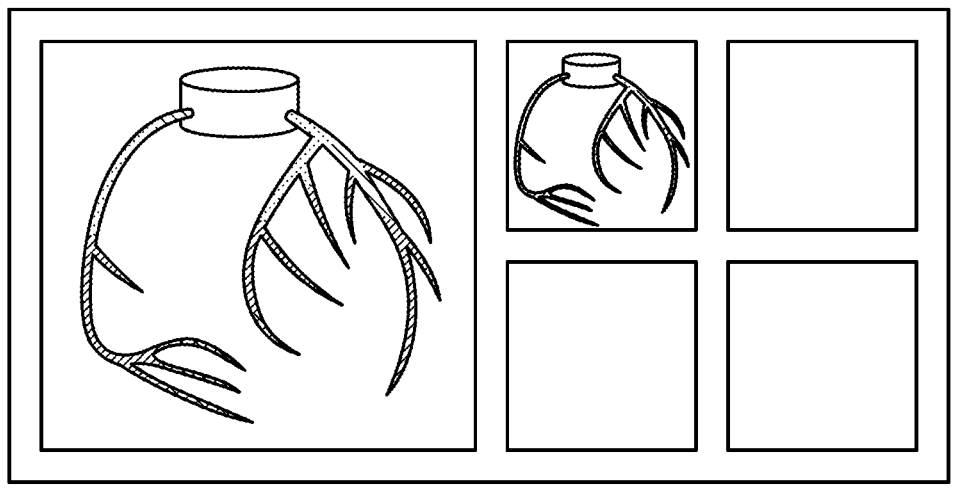
FIGS. 4A and 4B are diagrams illustrating examples of a WSS display image according to the first embodiment.

FIG. 4A is a diagram illustrating an example of a WSS display image according to the first embodiment. For example, as illustrated in FIG. 4A, the display control function 155e displays a color image formed when colors according to the WSS values are mapped in the VR image of the entire coronary artery of the selected subject. Herein, with respect to the VR image of the coronary artery, the display control function 155e can display a color image in which colors are assigned based on the result of the 1D-WSS, and can display a color image in which colors are assigned based on the result of the 3D-WSS.

For example, the display control function 155e extracts the center line of the blood vessels; generates a first-type display image (1D-WSS) in which one-dimensional information, which is obtained when the spatial distribution of the wall shear stress at all positions of the blood vessels is assigned for each position of the center line, is assigned to a three-dimensional image; generates a second-type display image (3D-WSS) in which three-dimensional information assigned to each spatial position of the blood vessels is assigned to a three-dimensional image; and displays the generated images. That is, at the time of displaying the 1D-WSS, the display control function 155e performs color mapping of the WSS spatial distribution, which is calculated according to the 1D-WSS and which does not have directional dependency in the blood vessel axis direction, in a three-dimensional blood vessel image. Moreover, at the time of displaying the 3D-WSS, the display control function 155e performs color mapping of the local-WSS spatial distribution, which is calculated according to the 3D-WSS and which is expressed in the form of a three-dimensional vector, in a three-dimensional blood vessel image.

Herein, the display state at the start of display can be set in an arbitrary manner. More particularly, at the start of display, the display control function 155e starts displaying a display image according to a preset angle and a preset magnification ratio. For example, the display control function 155e starts the display of the display image at a display angle set based on the WSS calculation result and the characteristics of the blood vessels. As an example, the display control function 155e starts the display at a display angle from which the position indicating the maximum WSS value or the position indicating the minimum WSS values is displayed.

Moreover, according to the size of the display area in which the display image is to be displayed, the display control function 155e can change the display form of the display image. More particularly, according to the size of the display area in which the display image is to be displayed, the display control function 155e can switch between displaying the 1D-WSS and displaying the 3D-WSS.

For example, if the size of the display area is greater than a predetermined size, then the display control function 155e displays a color image in which coloring is performed based on the result of the 3D-WSS. On the other hand, if the size of the display area is smaller than a predetermined size, then the display control function 155e displays a color image in which coloring is performed based on the result of the 1D-WSS.

Moreover, according to the size of the display area, the display control function 155e can change the blood vessel image to be displayed. For example, when the size of the display area is smaller than a predetermined size, the display control function 155e displays a color image formed when the WSS calculation result is reflected in the CPR image for each branch vessel.

Figure 4B:
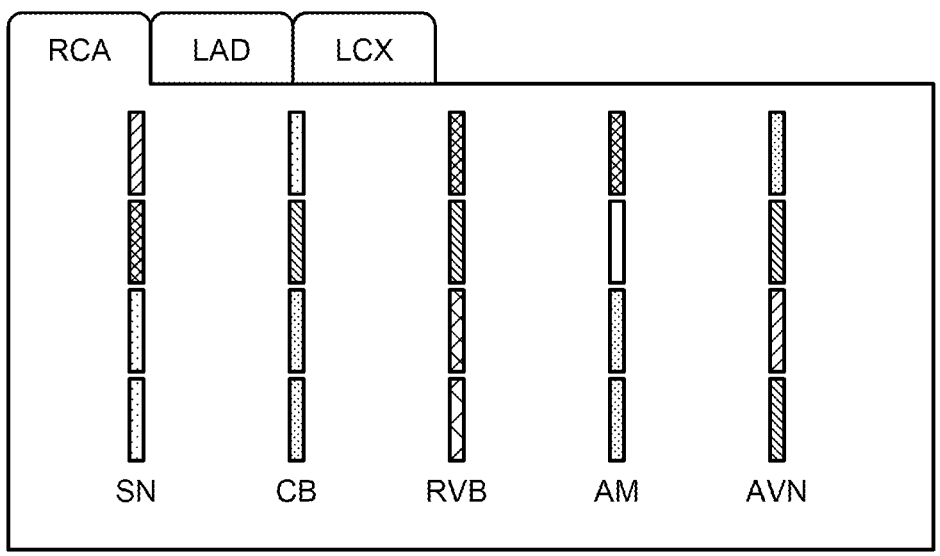

In that case, firstly, the display information generation function 155d uses the coronary CT image and generates a CPR image for each branch vessel. Then, the display control function 155e displays a display image in which the WSS values are reflected in the CPR images. As an example, as illustrated in FIG. 4B, the display control function 155e arranges the CPR images generated for each branch vessel in the "RCA", the "LAD", and the "LCX" of the coronary artery, and displays a display image in which the WSS values are reflected in the corresponding CPR images for each branch vessel.

Meanwhile, the size of the display area can be the size of the area assigned for displaying a display image in the display, or can be the size of the display screen itself in which a display image is to be displayed. For example, in the case of displaying a display image in a medical information display apparatus such as a tablet terminal or a smartphone, the size of the display screen of that apparatus can be treated as the size of the display area.

Rotational Display of WSS

As explained earlier with reference to Step S109 illustrated in FIG. 2, when a display image is displayed, according to the display method of the display image, the display control function 155e can switch between the display based on the 1D-WSS and the display based on the 3D-WSS.

For example, according to a user operation (for example, browsing or rotation) for changing the display position of the display image, the display control function 155e switches between the display based on the 1D-WSS and the display based on the 3D-WSS. As an example, at a timing at which the display position of the display image is changed, the display control function 155e performs the display based on the 1D-WSS; and, at a timing at which the display image is stationary, the display control function 155e performs the display based on the 3D-WSS.

For example, in the case of performing rotational display of the display image, the display control function 155e performs the display based on the 1D-WSS in which the spatial distribution of the WSS value at each position of the blood vessels is indicated as one-dimensional information in the image of the blood vessel. On the other hand, in the case of performing nonrotational display of the display image, the display control function 155e performs the display based on the 3D-WSS in which the spatial distribution of the WSS value at each position of the blood vessels is indicated as three-dimensional information in the image of the blood vessel.

Figure 5:
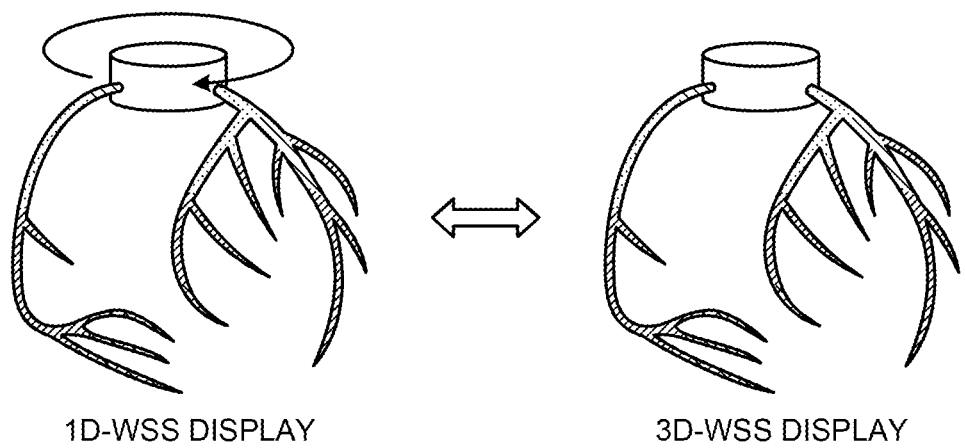
FIG. 5 is a diagram for explaining an example of switching between the display forms of a display image according to the first embodiment.

FIG. 5 is a diagram for explaining an example of switching between the display forms of a display image according to the first embodiment. In FIG. 5, the display form at the time of performing rotational display and the display form at the time of performing nonrotational display are illustrated. For example, as illustrated in the left side in FIG. 5, while the display position is being changed as a result of a rotation operation performed according to a user operation, the display control function 155e performs display based on the 1D-WSS. That is, according to a rotation operation performed by the user, the display control function 155e performs control to sequentially display color images formed when the result of the 1D-WSS is reflected in the VR image of the coronary artery that is rendered from the direction facing the user.

On the other hand, as illustrated in the right side in FIG. 5, while the color image is stationary without being subjected to any operation according to a user operation, the display control function 155e performs the display based on the 3D-WSS. That is, the display control function 155e performs control to continuously display a color image formed when the result of the 3D-WSS is reflected in the VR image of the coronary artery that is rendered from the direction facing the user.

For example, while the display image is being operated, it is important that the overall trend is understood; and, in the stationary state, it is necessary that a detailed study is done. Accordingly, the display control function 155e switches the display as explained above, and becomes able to display the display image that is appropriate for the situation. That enables achieving reduction in the time and efforts required by the user.

Meanwhile, performing the display based on the 3D-WSS generally results in an increase in the data volume. Hence, there is a possibility that the imaging speed slows down. However, at the time of operating the display image, it is necessary to switch the imaging at high speeds in order to enhance the usability. Hence, as explained above, while the display image is being operated, the display control function 155e performs the display based on the 1D-WSS, thereby enabling holding down a decline in the imaging speed.

In the example explained above, the display form is switched according to a user operation of the display image. Alternatively, the display control function 155e can automatically perform the rotational display using the cine mode display. For example, the display control function 155e performs control in such a way that, at the same time of starting the display at Step S108 illustrated in FIG. 2, the rotational display of the color image based on the 1D-WSS is also started. Subsequently, when a user operation for stopping the rotational display is received, the display control function 155e stopes the rotational display and switches to the display of the color image based on the 3D-WSS.

Herein, the display control function 155e can change the display form of the display image based on various conditions. More particularly, the display control function 155e can change the display form of the display image in a variety of ways based on the rotation condition of the display image, the display condition of the display image, and the WSS calculation result.

For example, in the case of using the rotation condition of the display image, the display control function 155e switches between the display based on the 1D-WSS and the display based on the 3D-WSS according to the rotation count and the rotation speed of the display image. As an example, if the rotation count or the rotation speed of the display image is equal to or smaller than a threshold value, then the display control function 155e performs the display based on the 3D-WSS. On the other hand, if the rotation count or the rotation speed of the display image is greater than the threshold value, then the display control function 155e performs the display based on the 1D-WSS.

Herein, the display control function 155e becomes able to perform display control in which the control based on rotation/nonrotation is combined with the control based on the rotation condition. For example, while the display based on the 1D-WSS is being performed during the rotational display, if the rotation speed is changed to be equal to or smaller than the threshold value, then the display control function 155e switches to the display based on the 3D-WSS. Moreover, while the display based on the 3D-WSS is being performed during the nonrotational display, if the condition is changed to start the rotation at a rotation speed equal to or smaller than a threshold value, then the display control function 155e continues with the display based on the 3D-WSS. Moreover, for example, during the rotational display, according to the rotation count and the rotation speed, the display control function 155e can change the type of the medical image (for example, a CT image) to be used as the display image. As an example, if at least either the rotation count or the rotation speed becomes equal to or smaller than the threshold value, then the display control function 155e displays the display image using a medical image of a predetermined type.

Moreover, for example, during the rotational display, according to the rotation angle, the display control function 155e can switch between the display based on the 1D-WSS and the display based on the 3D-WSS. As an example, during the rotational display of the coronary artery, the display control function 155e performs display based on the 3D-WSS for the coronary artery positioned close to the center of the display image, and performs display based on the 1D-WSS for the coronary artery positioned far from the center of the display image. For example, the coronary artery has three blood vessels, namely, the LAD, the LCX, and the RCA running around the heart. Thus, during the rotational display of the coronary artery, the display control function 155e performs display based on the 3D-WSS for the blood vessel that is close to the center in the display image, and performs display based on the 1D-WSS for the other blood vessels that are far from the center in the display image. That is, regarding each blood vessel of the coronary artery, when that blood vessel comes close to the center of the display image accompanying the rotation of the display image, the display control function 155e switches to the display based on the 3D-WSS; and, when that blood vessel moves away from the center of the display image, the display control function 155e switches to the display based on the 1D-WSS.

In this way, the coronary artery that is close to the center position to be focused can be displayed in a detailed 3D display. On the other hand, the coronary artery that is displayed to the side is purposely displayed in a 1D display without many details. That enables easier understanding of the overall trends, and enables achieving simplification of the display. Hence, even when the coronary artery displayed to the side does not have a favorable distribution of the values, it is prevented from being overlooked.

Meanwhile, for example, when the display condition of the display image is used, according to the magnification or reduction of a color image, the display control function 155e switches between the display based on the 1D-WSS and the display based on the 3D-WSS. As an example, if a color image is magnified by a magnification ratio exceeding a threshold value, then the display control function 155e performs the display based on the 3D-WSS. On the other hand, if a color image is reduced by a reduction ratio exceeding a threshold value, then the display control function 155e performs the display based on the 1D-WSS.

The display control function 155e can perform display control in which the control based on rotation/nonrotation is combined with the control based on the abovementioned display condition. For example, when the display based on the 1D-WSS is being performed during the rotational display, if the display image is magnified by a magnification ratio exceeding a threshold value, then the display control function 155e switches to the display based on the 3D-WSS. On the other hand, when the display based on the 3D-WSS is being performed during the nonrotational display, if the display image is reduced by a reduction ratio exceeding a threshold value, then the display control function 155e switches to the display based on the 1D-WSS. Moreover, for example, during the rotational display and the nonrotational display, if the display image is magnified or reduced, then the display control function 155e can change the type of the medical image (for example, a CT image) to be used as the display image. As an example, if a display image is magnified by a magnification ratio exceeding a threshold value or if a display image is reduced by a reduction ratio exceeding a threshold value, then the display control function 155e displays the display image using a medical image of a predetermined type.

Moreover, for example, in the case of using the WSS calculation result, regarding a position that is highly likely to be focused by the user (a position having a characteristic WSS, or a position at which plaque is present), the display control function 155e performs the display based on the 3D-WSS. As an example, when the rotational display based on the 1D-WSS is being performed, when a position having the WSS value to be equal to or greater than a threshold value or a position having the WSS value equal to or smaller than a threshold value moves closer to the front side of the screen, then the display control function 155e switches to the display based on the 3D-WSS. Moreover, for example, the display control function 155e identifies the positions of plaque or calcification in the coronary artery and, when an identified position comes close to the front side of the screen, switches to the display based on the 3D-WSS. As a method for identifying the positions of plaque and calcification in the coronary artery, the display control function 155e can appropriately implement any known method. Examples of that method include a method of performing image processing based on the distribution of pixel values, and a method using machine learning.

Rotation Speed

During the rotational display, the rotation speed can be appropriately varied according to various conditions. More particularly, the display control function 155e can arbitrarily vary the rotation speed during the rotational display based on the WSS calculation result and the characteristics of the blood vessels.

For example, in the case of using the WSS calculation result, during the rotational display, the display control function 155e performs control to reduce the rotation speed at the timings of displaying the positions of the blood vessels at which the maximum WSS value and the minimum WSS value are calculated. That is, the display control function 155e slows down the rotation when the positions having characteristic WSS values come close to the front side of the screen.

Figure 6:
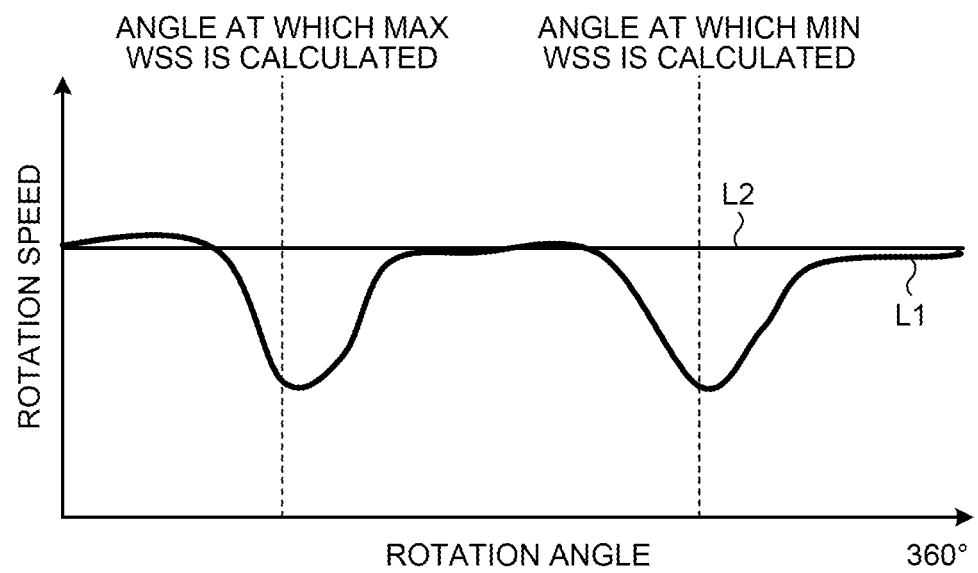
FIG. 6 is a diagram for explaining an example of the speed adjustment of the rotation speed according to the first embodiment.

FIG. 6 is a diagram for explaining an example of the speed adjustment of the rotation speed according to the first embodiment. In FIG. 6 is illustrated a graph in which the vertical axis represents the rotation speed and the horizontal axis represents the rotation angle. In FIG. 6, a curved line L1 represents the rotation speeds in the case in which characteristic WSS values are present in the WSS spatial distribution that is calculated, and a curved line L2 represents the rotation speeds in the case in which characteristic WSS values are not present in the WSS spatial distribution that is calculated.

For example, as indicated by the curved line L1 illustrated in FIG. 6, the display control function 155e reduces the rotation speed as the position indicating the maximum WSS value moves closer to the front side of the screen, and increases the rotation speed as the position indicating the maximum WSS value moves away from the front side of the screen. Moreover, as indicated by the curved line L1 illustrated in FIG. 6, the display control function 155e performs control to reduce the rotation speed as the position indicating the minimum WSS value moves closer to the front side of the screen, and performs control to increase the rotation speed as the position indicating the minimum WSS value moves away from the front side of the screen, so that the original rotation speed is restored.

Meanwhile, the speed adjustment of the rotation speed either can be performed using the maximum WSS value and the minimum WSS value in the entire coronary artery, or can be performed using the maximum WSS value and the minimum WSS value for each branch vessel of the coronary artery. Moreover, the speed adjustment of the rotation speed is not limited to be performed using the position indicating the maximum WSS value and the position indicating the minimum WSS value, and can also performed using the positions that indicate the WSS values equal to or greater than a threshold value and using the positions that indicate the WSS values equal to or smaller than the threshold value.

Meanwhile, if a characteristic WSS value is not present in the spatial distribution of the calculated WSS values, then the display control function 155e performs the rotational display of the display image at a constant rotation speed as indicated by the curved line L2 illustrated in FIG. 6.

In the case of using the characteristics of the blood vessels, during the rotational display, the display control function 155e performs control to reduce the rotation speed at the timing of displaying the position of a lesion area in the blood vessels. As an example, the display control function 155e performs control to reduce the rotation speed as a position at which plaque or calcification is detected moves closer to the front side of the screen, and performs control to increase the rotation speed as a position at which plaque or calcification is detected moves away from the front side of the screen, so that the original rotation speed is restored.

Figure 7:
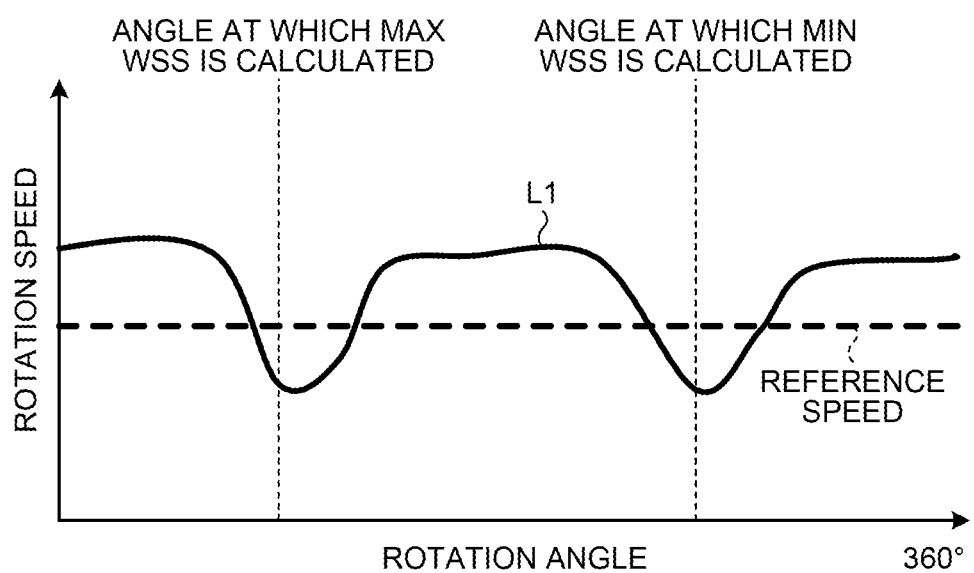
FIG. 7 is a diagram for explaining an example of the display control performed by a display control function according to the first embodiment.

Meanwhile, the display control function 155e can perform control with respect to a combination of adjusting the rotation speed and switching the display form (switching between the display based on the 1D-WSS and the display based on the 3D-WSS). FIG. 7 is a diagram for explaining an example of the display control performed by the display control function according to the first embodiment. In FIG. 7 is illustrated a case in which the switching of the display forms is combined with the speed adjustment performed with reference to the curved line L1 illustrated in FIG. 6.

For example, as illustrated in FIG. 7, a reference speed is set with respect to the rotation speed. The reference speed is set in arbitrary manner and, for example, is set in advance for each user or for each examination. When the rotation speed is higher than the reference speed, the display control function 155e performs display based on the 1D-WSS; and, when the rotation speed is lower than the reference speed, the display control function 155e performs display based on the 3D-WSS.

Operation for Controlling Display Direction

During the rotational display, the display direction can be appropriately varied according to various conditions. More particularly, based on the WSS calculation result and the characteristics of the blood vessels, the display control function 155e can arbitrarily vary the display direction during the rotational display of the display image.

For example, during the rotational display, as the position of a blood vessel at which the maximum WSS value or the minimum WSS value is calculated moves closer to the front side of the screen or as a lesion area in blood vessels moves closer to the front side of the screen, the display control function 155e adjusts the vertical direction of the rendering in such a way that the direction of travel of the blood vessels at that position is substantially parallel to the screen.

Display of Additional Information

During the display of a display image as explained above, it is possible to add a variety of additional information in the display image. More particularly, the display control function 155e can display a display image in which additional information regarding the WSS calculation result is added. More specifically, in a display image formed when the WSS value at each position of the blood vessels is reflected in a three-dimensional image, the display control function 155e adds information indicating the validness at each position at which the validness related to the calculation result is low.

For example, in the WSS calculation, due to the effect of the noise included in the image, sometimes the WSS cannot be calculated in some part of the image. In that regard, at the positions in the display image at which the WSS could not be calculated, the display control function 155e adds the additional information indicating that the WSS calculation was not successful.

Figure 8A:
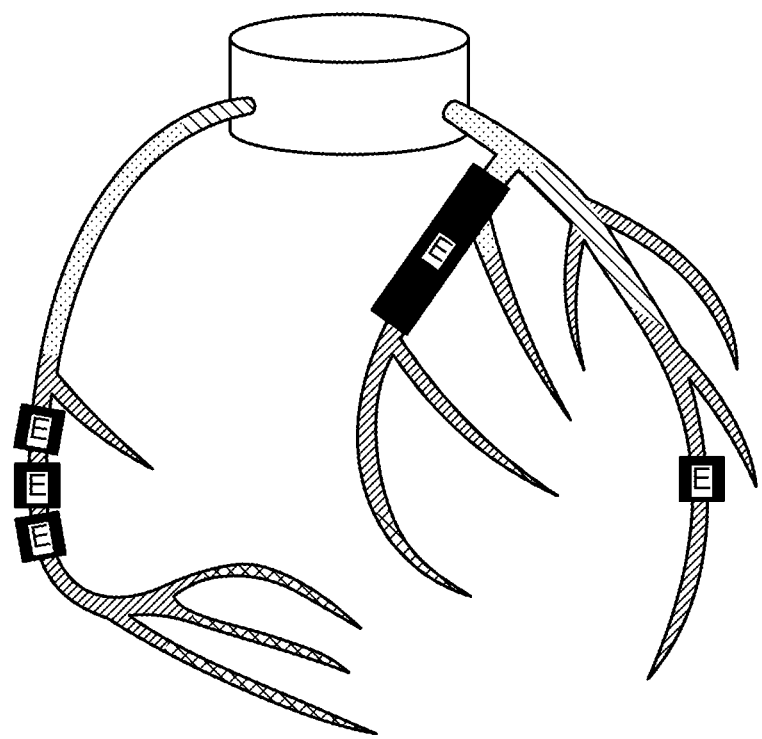
FIG. 8A is a diagram illustrating an exemplary display of additional information according to the first embodiment.

FIG. 8A is a diagram illustrating an exemplary display of additional information according to the first embodiment. For example, as illustrated in FIG. 8A, the display control function 155e displays the letter "E" indicating an error at each position at which the WSS could not be calculated.

Herein, the display control function 155e can control the display of the additional information in combination with controlling the rotational display. For example, during the rotational display of the display image, when a position at which the WSS could not be calculated moves closer to the front side of the screen, the display control function 155e displays the letter "E" indicating an error at that position. Moreover, during the rotational display of the display image, when a position at which the WSS could not be calculated moves away from the front side of the screen, the display control function 155e performs control to remove the letter "E" displayed at that position.

Meanwhile, the display control function 155e can control the display of the additional information in combination with controlling the rotation speed. For example, during the rotational display of the display image, the display control function 155e varies the rotation speed as a position at which the WSS could not be calculated moves closer to the front side of the screen.

Figure 8B:
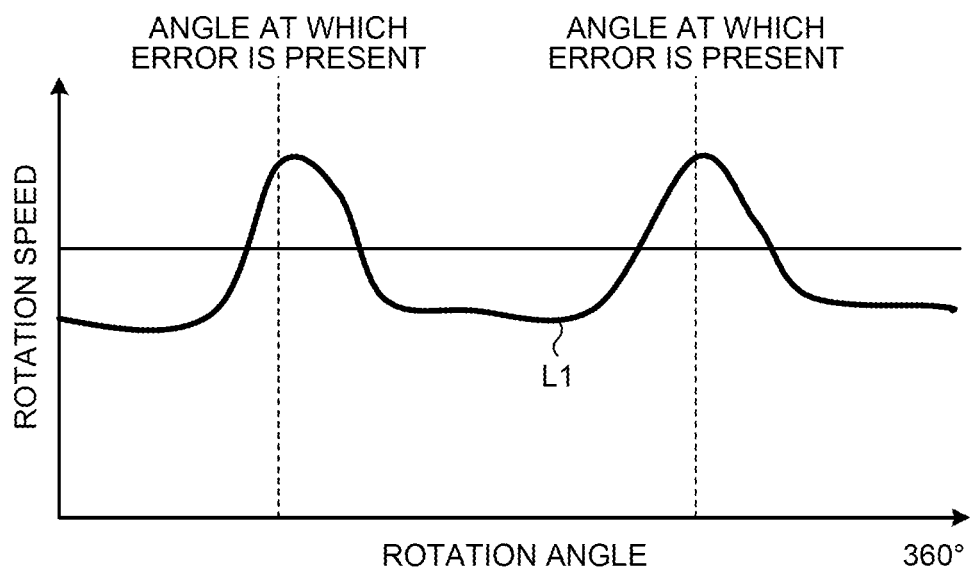
FIG. 8B is a diagram for explaining an example of controlling the rotation speed based on the additional information according to the first embodiment.

FIG. 8B is a diagram for explaining an example of controlling the rotation speed based on the additional information according to the first embodiment. In FIG. 8B is illustrated a graph in which the vertical axis represents the rotation speed and the horizontal axis represents the rotation angle. For example, the display control function 155e performs control to increase the rotation speed as a position having an error moves closer to the front side of the screen, and performs control to reduce the rotation speed as the position having an error moves away from the front side of the screen, so that the original rotation speed is restored.

Output of Calculation Result and Determination Result

The medical image processing apparatus 150 can output the calculation result and the determination result regarding the index value to various output destinations. More particularly, the control function 155f transfers the calculation result and the determination result regarding the index value to a predetermined destination.

Figure 9:
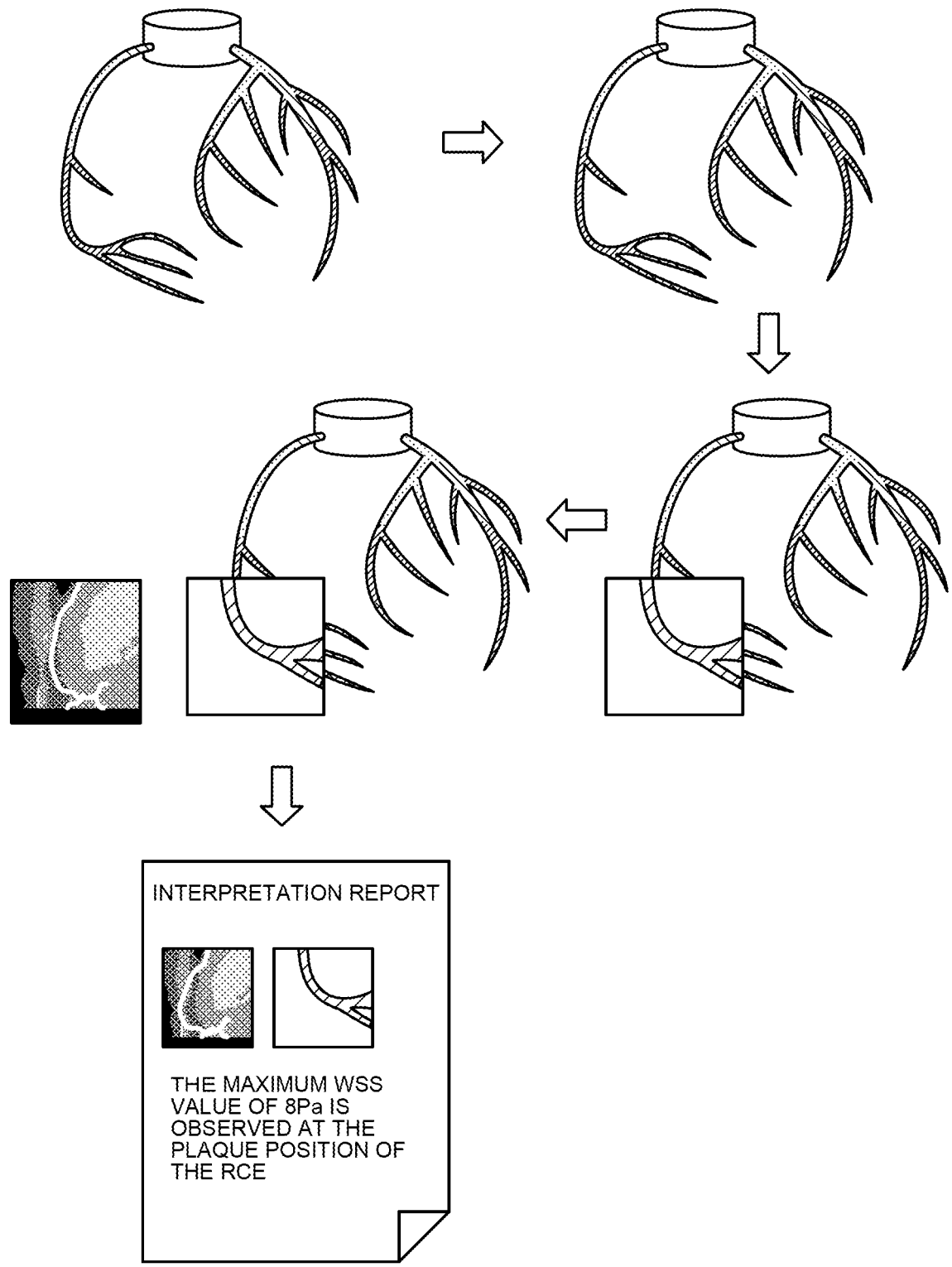
FIG. 9 is a diagram for explaining an example of the transfer of information as performed by a control function according to the first embodiment.

For example, the control function 155f can transfer the information regarding the WSS at the user-specified blood vessel position to various destinations. FIG. 9 is a diagram for explaining an example of the transfer of information as performed by the control function 155f according to the first embodiment. In FIG. 9 is illustrated the case in which the control function 155f transfers the information regarding the user-specified blood vessel position to an interpretation report.

For example, as illustrated in FIG. 9, firstly, the display control function 155e displays a VR image in the display 154. Herein, for example, the display control function 155e displays a color image in which coloring according to the WSS values is reflected in a VR image of the coronary artery, and performs rotational display of the color image. Then, using the input interface 153, the user performs a specification operation for specifying a position in the color image. In response, the display control function 155e displays a magnified image in which the specified position (region) is magnified.

As illustrated in FIG. 9, alongside the magnified image, the display control function 155e also displays a cross-sectional image of the original image corresponding to the specified position (region) (for example, displays an MPR image in the CT image). Thus, in response to various operations performed by the user, the display control function 155e displays a variety of information in the display 154.

Subsequently, when the user performs a transfer operation using the input interface 153, the information representing the target for the transfer operation is transferred to the destination. For example, as illustrated in FIG. 9, to an interpretation report, the control function 155f outputs the magnified image, the cross-sectional image, and information such as "the maximum WSS value of 8 Pa is observed at the plaque position of the RCE" indicating the WSS value at the specified blood vessel position.

Meanwhile, the information illustrated in FIG. 9 is only exemplary, and the control function 155f can transfer a variety of other information. For example, the control function 155f can transfer, to an interpretation report, the other characteristic WSS values (such as high WSS values or low WSS values), or the information regarding the WSS obtained from the form information of the coronary artery (for example, the distance from the bifurcation area of the coronary artery in the specified region, or the distance from large calcification).

Moreover, the control function 155f can transfer the calculated WSS values and the determination result to the medical image storage apparatus 120, the multi-department system 130, and the medical information display apparatus 140. For example, the control function 155f transfers the calculated WSS values to the viewer of the user, or to a workstation, or to an electronic health record system. Each apparatus holds the WSS values transferred thereto in an internal memory. Meanwhile, the control function 155f can transfer only the characteristic WSS values, from among the calculated WSS values, to the abovementioned apparatuses. Moreover, when a position of plaque is known in advance or when the coordinate information of plaque is already obtained and recorded using a known technology, the control function 155f can transfer the WSS value of only the position of plaque based on that information. Moreover, for example, the control function 155f can transfer the above-mentioned color image to a PACS.

The control function 155f can divide a variety of information on the basis of the branch vessels, and then transfer it. For example, the control function 155f sends, to various apparatuses in the network 160, the maximum WSS value and the minimum WSS value for each branch vessel of the coronary artery.

Moreover, according to the index values regarding the blood flow in the blood vessels, the control function 155f can change the destination for the WSS calculation result. In that case, the calculation function 155c simultaneously calculates the index values other than the WSS (for example, calculates the FFR). Then, according to the index values calculated in a simultaneous manner, the control function 155f changes the destination apparatus for transferring the WSS values.

As an example, when the FFR value is greater than a threshold value, the control function 155f transfers the WSS calculation result to a workstation meant for interpreting radiograms. On the other hand, when the FFR value is smaller than the threshold value, the control function 155f transfers the WSS calculation result to an electronic health record, the cellular phone of the doctor, or the email address of the doctor. Thus, when the FFR value is small and the degree of urgency is believed to be high, the control function 155f can promptly notify the doctor about the calculation result.

Moreover, the control function 155f can transfer the information regarding the WSS calculation to a 3D printer. In that case, for example, a 3D printer is connected to the network 160, and the control function 155f sends the form information of the coronary artery, which is calculated in the WSS calculation process, and the WSS calculation result to the 3D printer. At that time, depending on the WSS values, it can be determined whether or not to transfer them to a 3D printer. For example, control can be performed in such a way that, when the maximum WSS value is greater than a predetermined reference value, the WSS values can be transferred to a 3D printer; and, when the maximum WSS value is smaller than the predetermined reference value, the WSS values are not transferred to a 3D printer.

A 3D printer refers to the form information and the WSS calculation result, and generates a coronary artery model that is unique to the subject. For example, based on the received form information, the 3D printer generates a model of the coronary artery using predetermined materials (such as resin). At that time, the 3D printer generates a model using materials and colors according to the WSS values. The materials and the colors according to the WSS values are set in advance in the 3D printer.

Furthermore, the control function 155f transfers the WSS calculation result to a medical image diagnosis apparatus. For example, the control function 155f transfers the WSS calculation result to an intravascular ultrasound (IVUS) or to an intravascular imaging apparatus that is based on optical coherence tomography (OCT).

As an example, the control function 155f monitors registration information in the multi-department system 130, and determines whether or not a reservation is made for an IVUS or OCT. When a reservation is made for an IVUS or OCT, the control function 155f further determines whether or not information regarding the WSS is stored for the subject for which the reservation is made. If information regarding the WSS is stored for the subject, then the control function 155f obtains the stored information related to the WSS and transfers it to an intravascular imaging device.

Moreover, in response to a user operation, the control function 155f can obtain an image taken by an intravascular imaging apparatus, and display the image by superimposing the WSS information on it. In that case, firstly, the control function 155f obtains an image from the intravascular imaging apparatus, and performs position adjustment with the coronary CT image used in the WSS calculation. For example, the control function 155f performs position adjustment based on the anatomical features included in the image.

Then, based on the position adjustment result, the display control function 155e displays a display image formed when each position of the coronary artery in the image received from the intravascular imaging apparatus is superimposed with the corresponding WSS value. Moreover, the control function 155*f* transfers the display image, in which the WSS values are superimposed, to the intravascular imaging apparatus. As a result, the intravascular imaging apparatus becomes able to display an IVUS image or an OCT image in which the WSS values are specified.

Cooperation with Other Apparatuses

For example, the medical image processing apparatus 150 can perform operations in cooperation with other apparatuses in the network 160. For example, the control function 155*f* cooperates with an RIS and, when a reservation for a coronary CT image is made in the RIS, performs control to secure calculation resources for WSS calculation at the appointed timing. Meanwhile, at the point of time of a reservation, the control function 155*f* can receive input of the image size and various parameters. Moreover, the control function 155*f* can estimate the calculation end timing from the reservation information, and can send back the estimated calculation end timing to the user.

Moreover, based on the result of the calculated WSS values, the control function 155*f* makes a reservation for an examination apparatus or outputs a notification for prompting a reservation for an examination apparatus. For example, if a position at which plaque is present exhibits an extremely high WSS value, it is assumed that the subject corresponding to the image is at a high risk, and thus the control function 155*f* automatically makes a reservation for an intravascular OCT examination or makes a reservation for an operating room. Alternatively, for example, if a position at which plaque is present exhibits an extremely high WSS value, the control function 155*f* sends a notification to prompt the user to make a reservation for an intravascular OCT examination.

In the embodiment described above, the explanation is given about the case in which the control function 155*f* transfers the WSS calculation result to external apparatuses. However, the embodiment is not limited to that case. For example, in accordance with the WSS calculation result, the control function 155*f* can transfer the determination result obtained by the determination function 155*b*. That is, along with transferring the WSS calculation result, the control function 155*f* can also transfer the determination result about the validness of the calculation target and the determination result about the validness of the WSS calculation result.

Moreover, in the embodiment described above, the explanation is given about the case in which the determination operation is performed after obtaining the image data. However, the embodiment is not limited to that case. Alternatively, for example, firstly, the determination operation is performed, and then the image data of the target that satisfies the conditions can be obtained.

In that case, when the target image examination (for example, CT) is undertaken, the X-ray CT apparatus 110 transfers the imaging conditions to the medical image processing apparatus 150. Alternatively, the imaging conditions set in the RIS can be transferred to the medical image processing apparatus 150. The determination function 155*b* compares the transferred imaging conditions with predetermined conditions, and determines whether the transferred conditions are satisfied. Meanwhile, depending on the conditions that are set, the determination can be performed by obtaining information from the electronic health record. If it is determined that the imaging conditions are satisfied, then the obtaining function 155*a* requests the X-ray CT apparatus 110 or the medical image storage apparatus 120 to provide the corresponding image data.

As explained above, according to the first embodiment, the display information generation function 155*d* generates such a three-dimensional image of the blood vessels in which the WSS value at each position of the blood vessels is reflected. While displaying a display image that is a three-dimensional image in which the WSS values reflected, the display control function 155*e* changes the display form of the display image during the rotational display and during the nonrotational display. Hence, the medical image processing apparatus 150 according to the first embodiment can display the display image in an appropriate manner according to the situation, and enables achieving reduction in the time and efforts required by the user at the time of making the diagnosis related to heart illnesses and formulating a treatment plan.

Moreover, according to the first embodiment, when performing the rotational display of the display image, the display control function 155*e* displays the 1D-WSS in which the spatial distribution of the WSS values at all cross-sectional positions of the blood vessels with reference to the center line of the blood vessels is indicated in an image of the blood vessels. On the other hand, when performing the nonrotational display of the display image, the display control function 155*e* displays the 3D-WSS in which the spatial distribution of the WSS values at all positions in the blood vessels or on the vascular wall is indicated in an image of the blood vessels. Hence, the medical image processing apparatus 150 according to the first embodiment can automatically perform display in an appropriate manner during the rotational display and during the nonrotational display.

Furthermore, according to the first embodiment, according to the rotation condition for the display image, the display control function 155*e* further changes the display form of the display image. Hence, the medical image processing apparatus 150 according to the first embodiment can perform display in a more appropriate manner.

Moreover, according to the first embodiment, according to the display condition of the display image, the display control function 155*e* further changes the display form of the display image. Hence, the medical image processing apparatus 150 according to the first embodiment can perform display in a more appropriate manner.

Furthermore, according to the first embodiment, according to the size of the display area for displaying the display image, the display control function 155*e* further changes the display form of the display image. Hence, the medical image processing apparatus 150 according to the first embodiment can perform display in a more appropriate manner.

Moreover, according to the first embodiment, based on the WSS calculation result, the display control function 155*e* varies the rotation speed of the display image. Hence, the medical image processing apparatus 150 according to the first embodiment becomes able to perform the rotational display in a more easily observable manner.

Furthermore, according to the first embodiment, during the rotational display, the display control function 155*e* performs control to reduce the rotation speed at the timing of displaying the positions of the blood vessels at which the maximum WSS value and the minimum WSS value are calculated. Hence, in the medical image processing apparatus 150 according to the first embodiment, the positions to watch out for can be displayed at an easily observable rotation speed.

Moreover, according to the first embodiment, during the rotational display, the display control function 155*e* performs control to increase the rotation speed at the timing of displaying a position of the blood vessels at which the WSS calculation result is incorrect. Hence, in the medical image processing apparatus 150 according to the first embodiment, the positions that should be skipped for observation can be let through at a high rotation speed.

Furthermore, according to the first embodiment, based on the characteristics of the blood vessels, the display control function 155e varies the rotation speed of the display image. Hence, in the medical image processing apparatus 150 according to the first embodiment, the rotation speed can be varied at the positions to watch out for.

Moreover, according to the first embodiment, during the rotational display, the display control function 155e performs control to reduce the rotation speed at the timing of displaying the position of a lesion area in the blood vessels. Hence, in the medical image processing apparatus 150 according to the first embodiment, the lesion areas to watch out for can be made observable in an appropriate manner.

Furthermore, according to the first embodiment, in the WSS calculation, the determination function 155b determines the validness of the calculation target. The display control function 155e displays the determination result about the validness. Hence, in the medical image processing apparatus 150 according to the first embodiment, only the target having a high degree of reliability can be treated as the calculation target.

Moreover, according to the first embodiment, in the WSS calculation, the determination function 155b determines the validness of the calculation result. The display control function 155e displays the determination result about the validness of the calculation result. Hence, in the medical image processing apparatus 150 according to the first embodiment, only the result having a high degree of reliability can be taken into consideration.

Furthermore, according to the first embodiment, the display control function 155e displays a list indicating the WSS calculation result for each subject, and highlights such results in the list which have deviated from the reference value. Thus, the medical image processing apparatus 150 according to the first embodiment enables performing diagnosis using the results having high priority.

Moreover, according to the first embodiment, the display control function 155e further displays the analysis result other than the WSS in the list. Hence, the medical image processing apparatus 150 according to the first embodiment enables performing complex diagnosis.

Furthermore, according to the first embodiment, in the display image that is a three-dimensional image of the blood vessels in which the WSS value at each position of the blood vessels is reflected, the display control function 155e adds information indicating the validness at the positions having low validness related to the calculation result. Hence, the medical image processing apparatus 150 according to the first embodiment enables understanding, in one glance, the positions having the results of a low degree of reliability.

Moreover, according to the first embodiment, the calculation function 155c calculates the WSS value at each position of the blood vessels. The control function 155f transfers the WSS calculation result to predetermined destinations. Hence, the medical image processing apparatus 150 according to the first embodiment enables the transfer of the WSS result to various destinations.

Furthermore, according to the first embodiment, the control function 155f transfers the WSS calculation result to a medical report. Hence, the medical image processing apparatus 150 according to the first embodiment enables achieving reduction in the time and efforts required in creating a medical report.

Moreover, according to the first embodiment, the control function 155f transfers the information regarding the WSS calculation to a 3D printer. Hence, the medical image processing apparatus 150 according to the first embodiment enables easy generation of a model based on the WSS result.

Furthermore, according to the first embodiment. The control function 155f transfers the WSS calculation result to a medical image diagnosis apparatus. Hence, the medical image processing apparatus 150 according to the first embodiment enables reflection of the WSS result in medical images.

Moreover, according to the first embodiment, according to the index values related to the blood flow in the blood vessels, the control function 155f changes the destination for the WSS calculation result. Hence, the medical image processing apparatus 150 according to the first embodiment can transfer the WSS result to an appropriate destination according to the index values.

Furthermore, according to the first embodiment, based on the WSS calculation result, the control function 155f outputs a reservation for an examination apparatus or a notification prompting reservation for an examination apparatus. Hence, in the medical image processing apparatus 150 according to the first embodiment, according to the WSS result, the subsequent necessary arrangements can be performed with certainty.

Moreover, according to the first embodiment, according to a reservation made for the collection of medical image data to be used in WSS calculation, the control function performs control to secure the calculation resources for WSS calculation. Hence, the medical image processing apparatus 150 according to the first embodiment can smoothly implement the schedule related to WSS calculation.

Second Embodiment

In the first embodiment described above, the explanation is given for the case in which, every time the image data is collected, the WSS is calculated in advance. In a second embodiment, the explanation is given for a case in which the WSS is calculated in response to a user instruction. Meanwhile, in the medical image processing apparatus 150 according to the second embodiment, the operation details of the display control function 155e are different as compared to the first embodiment. Thus, the following explanation is given with a focus on those differences.

Figure 10:
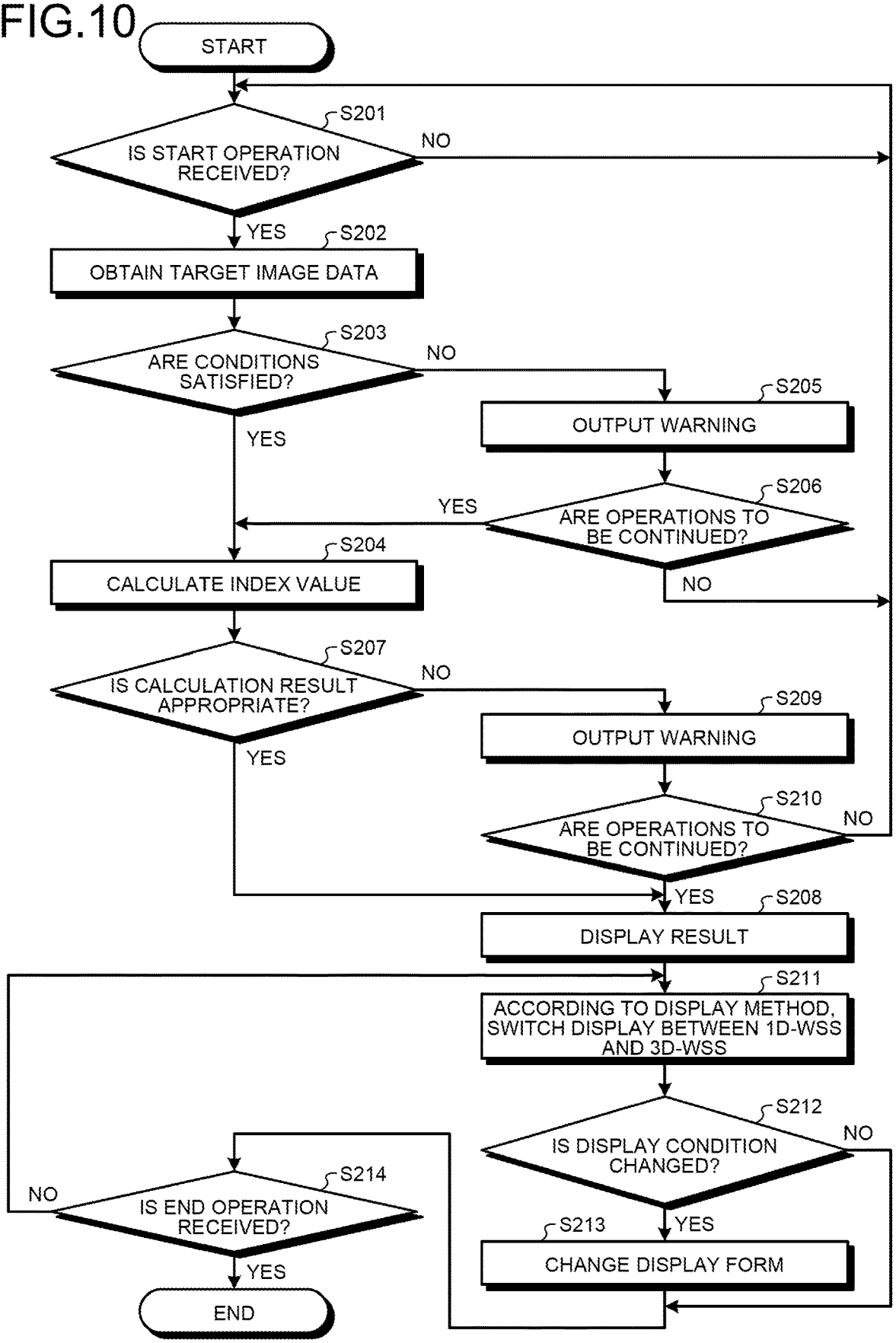
FIG. 10 is a flowchart for explaining the sequence of operations performed by the processing functions of the processing circuitry in the medical image processing apparatus according to a second embodiment.

Firstly, explained below with reference to FIG. 10 is the sequence of operations performed by the medical image processing apparatus 150 according to the second embodiment. FIG. 10 is a flowchart for explaining the sequence of operations performed by the processing functions of the processing circuitry 155 in the medical image processing apparatus 150 according to the second embodiment. With reference to FIG. 10, the explanation is given for the case in which the WSS is calculated in response to a WSS calculation instruction issued by the user.

For example, as illustrated in FIG. 10, in the second embodiment, when a start operation is received via the input interface 153 (Yes at Step S201), the obtaining function 155a obtains a coronary CT image of the specified subject from the X-ray CT apparatus 110 or the medical image storage apparatus 120 (Step S202). This operation is implemented when, for example, the processing circuitry 155 calls the computer program corresponding to the obtaining function 155a from the memory 152 and executes it. Meanwhile, until a start operation is received via the input interface 153, the standby state is maintained (No at Step S201).

Then, the determination function 155b determines whether or not the conditions are satisfied when the obtained coronary CT image is treated as the target (Step S203). More particularly, the determination function 155*b* determines whether or not the obtained coronary CT image has validness as the target for WSS calculation. This operation is implemented when, for example, the processing circuitry 155 calls the computer program corresponding to the determination function 155*b* from the memory 152 and executes it.

If the determination function 155*b* determines that the conditions are satisfied (Yes at Step S203), then the system control proceeds to Step S204. On the other hand, if the determination function 155*b* determines that the conditions are not satisfied (No at Step S203), then the system control proceeds to Step S205.

At Step S205, the display control function 155*e* outputs a warning (Step S205). For example, the display control function 155*e* displays, in the display 154, a warning indicating that the obtained coronary CT image does not have validness as the target for WSS calculation. This operation is implemented when, for example, the processing circuitry 155 calls the computer program corresponding to the display control function 155*e* from the memory 152 and executes it.

Subsequently, the calculation function 155*c* determines whether or not to continue the operations (Step S206). For example, the calculation function 155*c* determines whether continuation or termination is instructed via the input interface 153. This operation is implemented when, for example, the processing circuitry 155 calls the computer program corresponding to the calculation function 155*c* from the memory 152 and executes it.

If the calculation function 155*c* determines that the operations are to be continued (Yes at Step S206), then the system control proceeds to Step S204. On the other hand, if the calculation function 155*c* determines that the operations are not to be continued (No at Step S206), then the system control returns to Step S201 and the determination operation is performed.

At Step S204, the calculation function 155*c* calculates an index value related to the blood flow based on the coronary CT image of the subject as obtained by the obtaining function 155*a* (Step S204). For example, the calculation function 155*c* calculates the WSS. This operation is implemented when, for example, the processing circuitry 155 calls the computer program corresponding to the calculation function 155*c* from the memory 152 and executes it.

Subsequently, the determination function 155*b* determines whether or not the calculation result is appropriate (Step S207). More particularly, the determination function 155*b* determines whether or not the WSS calculation result obtained by the calculation function 155*c* has validness. This operation is implemented when, for example, the processing circuitry 155 calls the computer program corresponding to the determination function 155*b* from the memory 152 and executes it.

If the determination function 155*b* determines that the calculation result is appropriate (Yes at Step S207), then the system control proceeds to Step S208. On the other hand, if the determination function 155*b* determines that the calculation result is not appropriate (No at Step S207), then the system control proceeds to Step S209.

At Step S209, the display control function 155*e* outputs a warning (Step S209). For example, the display control function 155*e* displays, in the display 154, a warning indicating that the calculated WSS values are not valid. This operation is implemented when, for example, the processing circuitry 155 calls the computer program corresponding to the display control function 155*e* from the memory 152 and executes it.

Then, the display control function 155*e* determines whether or not to continue the operations (Step S210). For example, the display control function 155*e* determines whether continuation or termination is instructed via the input interface 153. This operation is implemented when, for example, the processing circuitry 155 calls the computer program corresponding to the display control function 155*e* from the memory 152 and executes it.

If the display control function 155*e* determines that the operations are to be continued (Yes at Step S210), then the system control returns to Step S208. On the other hand, if the display control function 155*e* determines that the operations are not to be continued (No at Step S210), then the system control returns to Step S201 and the determination operation is performed.

At Step S208, the display information generation function 155*d* generates display information regarding the result, and the display control function 155*e* displays the generated display information in the display 154 (Step S208). This operation is implemented when, for example, the processing circuitry 155 calls the computer programs corresponding to the display information generation function 155*d* and the display control function 155*e* from the memory 152 and executes them.

Subsequently, according to the display method, the display control function 155*e* switches between the 1D-WSS and the 3D-WSS (Step S211). For example, the display control function 155*e* changes the display form in such a way that the 1D-WSS is displayed during the rotational display and the 3D-WSS is displayed during the nonrotational display. This operation is implemented when, for example, the processing circuitry 155 calls the computer program corresponding to the display control function 155*e* from the memory 152 and executes it.

Then, the display control function 155*e* determines whether or not the display condition has changed (Step S212). For example, the display control function 155*e* determines whether or not the rotation condition or the display condition has changed. As an example, the display control function 155*e* determines whether or not the rotation condition including at least either the rotation count or the rotation speed has changed, or whether or not the display condition including magnification or reduction has changed. If the display condition has changed (Yes at Step S212), then the display control function 155*e* changes the display form (Step S213). On the other hand, if the display condition has not changed (No at Step S212), then the system control proceeds to Step S214.

Subsequently, the display control function 155*e* determines whether or not an end operation is received via the input interface 153 (Step S214). If an end operation is received (Yes at Step S214), then the medical image processing apparatus 150 ends the operations. On the other hand, if an end operation is not received (No at Step S214), then the system control returns to Step S211 and the switching display is continued.

Warning Display

As explained above, the display control function 155*e* outputs warnings according to the result of the determination operations performed by the determination function 155*b*. For example, in the display 154, the display control function 155*e* can display a warning according to each determination result, and can display the information notifying whether or not different image data is to be obtained.

Moreover, for example, the display control function 155e can display a warning also when any difficult-to-predict phenomenon, such as power outage or computer malfunctioning, occurs because of which the calculation is not completed in a normal manner.

Moreover, in addition to displaying a warning, the display control function 155e can automatically search the medical image storage apparatus 120 or the X-ray CT apparatus 110 in the network 160 for the images satisfying the conditions, and can present those images as candidate images. In that case, the determination function 155b performs a determination operation with respect to the image data of the same subject that is stored in the medical image storage apparatus 120 or the X-ray CT apparatus 110, and extracts image data satisfying the conditions. Then, the display control function 155e displays the information regarding the extracted image data (displays the candidate targets for calculation) in the display 154. Herein, as far as the determination conditions applied by the determination function 155b are concerned, it is also possible to have the case in which the conditions for candidate presentation are newly set. For example, the conditions for candidate presentation can be set based on the magnitude of effect with respect to the degree of calculation accuracy in the WSS calculation.

Moreover, in addition to displaying a warning regarding the WSS, the display control function 155e can display warnings regarding other index values too. For example, regarding a calculation value (such as the FFR) that is calculated in a similar manner to the WSS, since the calculation result is highly likely to indicate a problem, the display control function 155e performs display to draw attention to it.

The determination function 155b according to the second embodiment performs the determination operation in an identical manner to the first embodiment.

As explained above, according to the second embodiment, the display control function 155e displays a warning according to the determination of the validness of the calculation target and a warning according to the validness of the WSS calculation result. Hence, the medical image processing apparatus 150 according to the second embodiment enables efficient calculation of the WSS.

Third Embodiment

In a third embodiment, the explanation is given about various forms at the time of displaying a cross-sectional image indicating a cross-sectional surface of the blood vessels. For example, the display control function 155e according to the third embodiment displays a display image formed when the WSS values are assigned to a cross-sectional image indicating a cross-sectional surface of the blood vessels. The input interface 153 receives an input operation for moving the position of the cross-sectional surface that is displayed as the display image. Thus, based on the WSS calculation result, the display control function 155e varies the movement speed of the position of the cross-sectional surface according to the input operation.

Figure 11:
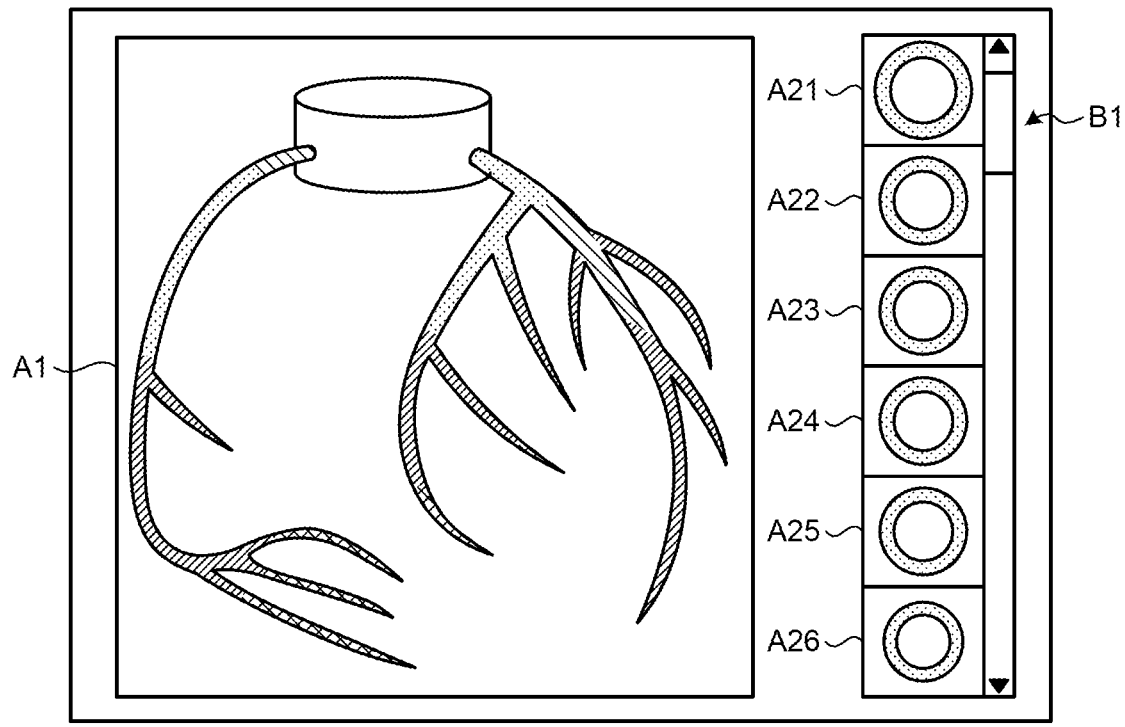
FIG. 11 is a diagram for explaining an example of the display control performed by a display control function according to a third embodiment.

FIG. 11 is a diagram for explaining an example of the display control performed by a display control function according to the third embodiment. With reference to FIG. 11, the explanation is given about the case in which short axis plane images (crosscut images) are displayed that represent the cross-sectional surfaces orthogonal to the center line of the blood vessels. For example, as illustrated in FIG. 11, the display control function 155e displays, in a display area A, a VR image of the coronary artery; and displays, in display areas A21 to A26, short axis plane images at all positions of the coronary artery. Meanwhile, the display control function 155e can display an image in which each pixel of the short axis plane images are represented according to the WSS values corresponding to each pixel position. For example, the display control function 155e can display a color image in which each pixel of the short axis plane images are represented colors according to the WSS values. In addition, the display control function 155e may display an image represented by transparency, lightness, grayscale value, texture, symbol, mark and so on, according to the WSS values. Furthermore, the display control function 155e may display any images as long as it is an image represented by an expression method according to the WSS values.

The input interface 153 receives a scroll operation with respect to a scrollbar B1. The scrollbar B1 illustrated in FIG. 11 represents a GUI that enables switching among the short axis plane images displayed in the display areas A21 to A26. That is, the user can operate the scrollbar B1 using the input interface 153, and switch among the short axis plane images, which are displayed in the display areas A21 to A26, along the center line of the coronary artery. The following explanation is given for an example in which a speed of switching among the short axis plane images is specified by a user input operation through the input interface 153.

Firstly, an explanation is given about the switching among the short axis plane images by operating the scrollbar B1. The user operates a mouse pointer displayed on the screen by using the input interface 153. An icon (a part that is displayed as a rectangle in the scrollbar B1) is shown in the scrollbar B1, which conceptually indicates which position of the blood vessel to be displayed corresponds to the short axis plane images displayed in the display areas A21 to A26. That is, when the icon is at a top of the scrollbar B1, the short axis plane images near proximal of the blood vessel are displayed, and when the icon is at a bottom of the scrollbar B1, the short axis plane images near distal of the blood vessel are displayed. The user specifies a destination of the icon by dragging the icon with the mouse pointer. The display control function 155e sequentially switches and displays the short axis plane images that are already displayed in the display areas A21 to A26 to short axis plane images that are not displayed according to the destination of the specified icon. Specifically, the display control function 155e repeats switching of displaying the short axis plane image at position of the display area A22 in the display area A21 and the short axis plane image at position of the display area A23 in the display area A22. As a result, the display control function 155e causes the display area A26 to display a short axis plane image that was not displayed at the start of the input operation. The display control function 155e performs switching display to the short axis plane images that were not displayed by executing the switching in this way, displays the short axis plane images corresponding to the position of the icon specified by the user in the display areas A21 to A26, and ends the switching.

In this switching operation, instead of dragging the icon, an arbitrary position on the scrollbar B1 is specified by the mouse pointer, and the icon is moved to the specified position by clicking the mouse to confirm the position. At the same time, the short axis plane images may be switched in conjunction with the scrolling movement of the icon.

Next, an explanation is given about the switching speed among the short axis plane images. As described above, the user switches the display to the short axis plane image that was not displayed at the start of the input operation by performing the operation on the scrollbar B1. The speed of this switching display becomes faster as a distance between a position of the icon at the start of the input operation and a position of the movement destination of the icon specified by the user by a drag operation or the like increase, and becomes slower as the distance becomes shorter.

Herein, during the switching display of the short axis plane images according to the operation of the scrollbar B1; based on the WSS calculation result, the display control function 155e according to the third embodiment varies the switching speed of the position of the cross-sectional surface according to the input operation. For example, at the time of displaying the short axis plane images at the positions of the blood vessels at which the maximum WSS value and the minimum WSS value are calculated, the display control function 155e reduces the switching speed of the corresponding short axis plane images in the display areas A21 to A26. Meanwhile, in an identical manner to the conditions for controlling the rotation speed during the rotational display as explained in the first embodiment, the display control function 155e according to the third embodiment can vary the switching speed of the short axis plane images in the display areas A21 to A26 based on the positions at which the WSS calculation result is incorrect, based on the characteristics of the blood vessels, and based on the positions of the lesion areas.

Moreover, during the display of the short axis plane images, according to the switching speed of the short axis plane images according to the input operation, the display control function 155e according to the third embodiment can change the display form of the display image. For example, when the user operates the scrollbar B1 using the input interface 153 and switches among the short axis plane images, which are displayed in the display areas A21 to A26, along the center line of the coronary artery; if the scroll bar B1 is scrolled at a speed equal to or higher than a predetermined threshold value, then the display control function 155e displays the short axis plane images as an image in which each pixel of the short axis plane images are represented colors according to the values of the 1D-WSS. On the other hand, if the scrollbar B1 is scrolled at a speed lower than the predetermined threshold value, then the display control function 155e displays the short axis plane images as an image in which each pixel of the short axis plane images are represented colors according to the values of the 3D-WSS.

Figure 12:
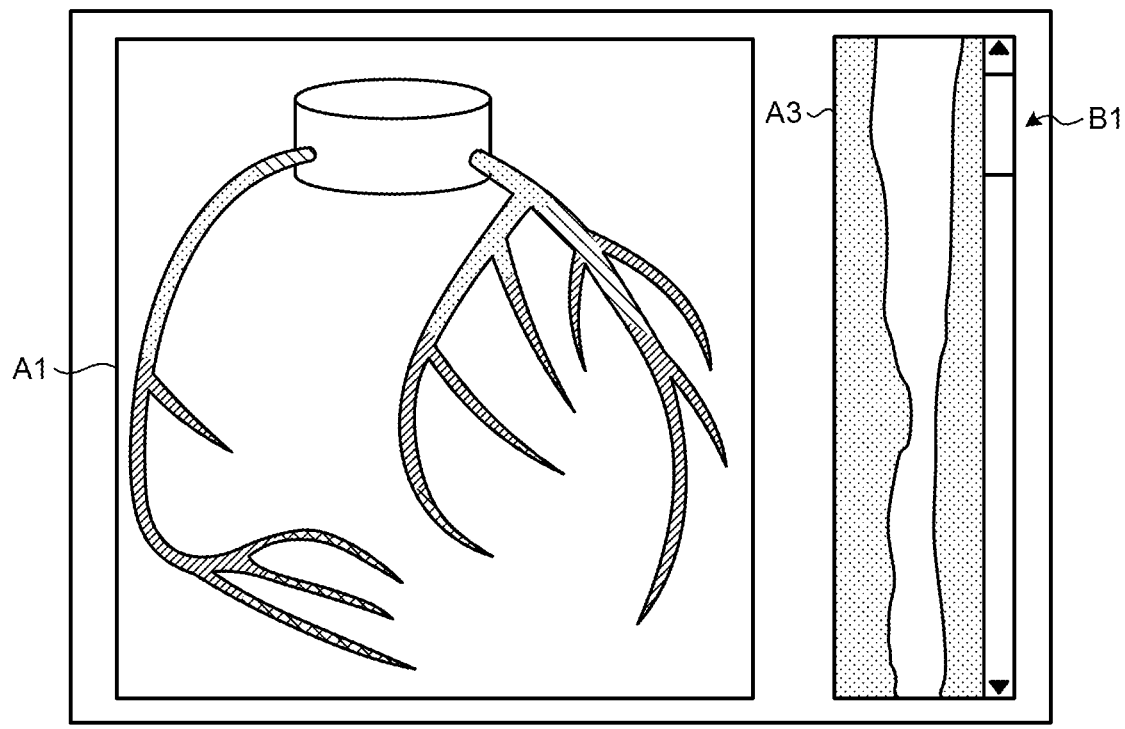
FIG. 12 is a diagram for explaining an example of the display control performed by the display control function according to the third embodiment.

In the example given above, the explanation is given about the case in which short axis plane images are displayed as the cross-sectional surfaces of the blood vessels. Alternatively, the display control function 155e can display CPR images as the medical images indicating the cross-sectional surfaces of the blood vessels. FIG. 12 is a diagram for explaining an example of the display control performed by the display control function according to the third embodiment. For example, as illustrated in FIG. 12, the display control function 155e displays a VR image of the coronary artery in the display area A1, and displays a CPR image of the coronary artery in a display area A3. As with the short axis plane images, the display control function 155e can display each pixels of the CPR images as an image expressed according to a value corresponding to each position.

Herein, in an identical manner to the display of the short axis plane images; based on the WSS calculation result, the display control function 155e varies, in the CPR image too, the switching speed of the position of the cross-sectional surface according to the input operation. In that case, for example, the scrollbar B1 represents a GUI that enables switching the position of the CPR image, which is displayed in the display area A3, along the direction of travel of the blood vessels.

During the switching display of the display position of the CPR image according to the operation of the scrollbar B1 as illustrated in FIG. 12; based on the WSS calculation result, the display control function 155e varies the switching speed of the position according to the input operation. For example, when the positions at which the WSS maximum value and the WSS minimum value are calculated are displayed in the CPR image, the display control function 155e lowers the switching speed of the CPR image within the display area A3. Meanwhile, during the display of a CPR image too, in an identical manner to the control conditions for the rotation speed during the rotational display as explained in the earlier embodiments, the display control function 155e according to the third embodiment can vary the switching speed based on the positions at which the WSS calculation result is incorrect, based on the characteristics of the blood vessels, and based on the positions of the lesion areas.

Moreover, during the display of a CPR image too, the display control function 155e according to the third embodiment can change the display form of the display image according to the switching speed of the position as based on the input operation. For example, when the user operates the scrollbar B1 using the input interface 153 and changes the position of the CPR image displayed in the display area A3, if the scrollbar B1 is scrolled at a speed equal to or higher than a predetermined threshold value, then the display control function 155e displays the CPR image as an image in which each pixel of the CPR image are represented colors according to the values of the 1D-WSS On the other hand, if the scrollbar B1 is scrolled at a speed lower than the predetermined threshold value, then the display control function 155e displays the CPR image as an image in which each pixel of the CPR image are represented colors according to the values of the 3D-WSS.

As explained above, according to the third embodiment, the display control function 155e displays a display image formed when the WSS values are assigned to a cross-sectional image indicating a cross-sectional surface of the blood vessels. The input interface 153 receives the input operation for changing the position of the cross-sectional surface being displayed as the display image. Based on the WSS calculation result, the display control function 155e varies the changing speed of the position of the cross-sectional surface according to the input operation. Hence, the medical image processing apparatus 150 according to the third embodiment enables the user to easily understand the position of the cross-sectional surface on which the attention should be focused.

Moreover, according to the third embodiment, the display control function 155e displays a display image formed when the WSS values are assigned to a cross-sectional image indicating a cross-sectional surface of the blood vessels. The input interface 153 receives an input operation for changing the position of the cross-sectional surface being displayed as the display image. The display control function 155e changes the display form of the display image according to the changing speed of the position of the cross-sectional surface based on the input operation. Hence, the medical image processing apparatus 150 can appropriately display the WSS according to the speed of change of the display position of the cross-sectional image.

Other Embodiments

In the embodiments described above, the explanation is given about the case in which, as the display form during the rotational display, the 1D-WSS is used in which the WSS at each cross-sectional position of the blood vessels is indicated with reference to the center line of the blood vessels. However, the embodiments are not limited by that example. Alternatively, for example, the directional average value of the local WSS as obtained from the 3D-WSS can be used, and a display equivalent to the 1D-WSS can be performed.

Moreover, in the embodiments described above, the explanation is given about the case in which the WSS-related information is displayed in the display 154 of the medical image processing apparatus 150. However, the embodiments are not limited by that example. Alternatively, for example, the WSS-related information can be displayed in the display of the medical information display apparatus 140.

Furthermore, in the embodiments described above, the explanation is given about the case in which the WSS calculation and the display of the calculation result is performed by the medical image processing apparatus 150. However, the embodiments are not limited by that example. For example, at the time of calculating the 1D-WSS and the 3D-WSS, a computer configuration of the server-client type can be adapted, and some part of the calculation can be performed in the server. For example, the 3D-WSS having a large calculation amount can be calculated in the server, and the 1D-WSS can be calculated in the client.

Meanwhile, for example, the processes up to recognizing (extracting) the characteristics of the blood vessels can be performed in the client, and only the process of calculating the WSS using the CFD can be performed in the server. In that case, instead of transferring the entire image to the server, only the form structure extracted in the client can be transferred to the server. For example, the server stores therein the analysis conditions in advance, and performs the WSS calculation using the form structure received from the client and using the stored analysis conditions.

Moreover, for example, in addition to transferring the form information, the client can also transfer, to the server, the subject-specific parameters of the blood flow (such as the hematocrit value), the environment conditions, and the coefficient of flexibility of the vascular wall. Then, the server calculates the WSS using such information transferred from the client.

Herein, regarding the structure information of the blood vessels, the same values can be set for each structure and only the data associated to the coordinates can be sent, so that the data size can be significantly reduced by data compression. For example, if it is assumed to have two types of structures, namely, the vascular wall and the structure other than the vascular wall, then the structures can be expressed as binary values of 0 and 1. In an identical manner, if there are 10 types of structures, they can be expressed using decimal values from 0 to 9.

In this way, if only the data required in calculation is communicated between a server and a client, then the transfer speed and the calculation cost in the server can be reduced. Meanwhile, the configuration can be such that the branch vessels to be calculated in the server are identified based on a user instruction, and the WSS of only those branch vessels are calculated.

In the embodiments described above, the explanation is given about the case in which the determining unit, the calculating unit, the generating unit, the display control unit, and the control unit mentioned in the written description are implemented using the determination function, the calculation function, the display information generation function, the display control function, and the control function, respectively, of a control circuit. However, the embodiments are not limited by that example. For example, apart from implementing the determining unit, the calculating unit, the generating unit, the display control unit, and the control unit mentioned in the written description using the determination function, the calculation function, the display information generation function, the display control function, and the control function, respectively; they can be implemented using only hardware, or using only software, or using a combination of hardware and software.

In the explanation of the embodiments, the term "processor" implies, for example, a central processing unit (CPU); or a graphics processing unit (GPU); or a circuit such as an application specific integrated circuit (ASIC) or a programmable logic device (such as a simple programmable logic device (SPLD), a complex programmable logic device (CPLD), or a field programmable gate array (FPGA)). Meanwhile, instead of storing computer programs in a memory circuit, they can be directly embedded into the circuit of a processor. In that case, the processor reads the computer programs embedded in the circuit and executes them so as to implement the functions. Meanwhile, a processor according to the embodiment is not limited to be configured using a single independent circuit. Alternatively, a single processor can be configured by combining a plurality of independent circuits in which the functions are implemented.

The computer program that is executed by a processor is stored in advance in a read only memory (ROM) or a memory circuit. Alternatively, the computer program can be recorded as an installable file or an executable file in a computer-readable non-transitory memory medium such as a compact disk read only memory (CD-ROM), a flexible disk (FD), a compact disk recordable (CD-R), or a digital versatile disk (DVD). Still alternatively, the computer program can be stored in downloadable manner in a computer connected to a network such as the Internet. For example, the computer program can have a modular configuration including the processing functions explained above. As far as the actual hardware is concerned, a CPU reads the computer program from a memory medium such as a ROM and executes it, so that the modules are loaded and generated in a main memory.

Meanwhile, in the embodiments and the modification examples thereof, the constituent elements of the apparatus illustrated in the drawings are merely conceptual, and need not be physically configured as illustrated. The constituent elements, as a whole or in part, can be separated or integrated either functionally or physically based on various types of loads or use conditions. Moreover, the process functions performed by the apparatus are entirely or partially implemented by the CPU or computer programs that are analyzed and executed by the CPU, or implemented as hardware by wired logic.

Moreover, Of the processes described in the embodiments and the modification examples thereof, all or part of the processes explained as being performed automatically can be performed manually. Similarly, all or part of the processes explained as being performed manually can be performed automatically by a known method. The processing procedures, the control procedures, specific names, various data, and information including parameters described in the embodiments or illustrated in the drawings can be changed as required unless otherwise specified.

According to at least one of the embodiments described above, it becomes possible to reduce the time and efforts required by the user at the time of performing diagnosis related to heart illnesses and formulating a treatment plan.

In regard to the embodiments, the following notes are disclosed as aspects of the present invention and as selective features.

(Note 1)
A medical image processing apparatus including:
an obtaining unit that obtains a three-dimensional image of a blood vessel of a subject and obtains spatial distribution of values of wall shear stress at each position of the blood vessel;
a display control unit that displays, from an arbitrary angle, a display image formed by assigning the values of the wall shear stress to the three-dimensional image; and
an input operation receiving unit that receives an input operation for changing the angle, wherein
during display of the display image formed by assigning the values of the wall shear stress to the three-dimensional image, the display control unit changes display form of the display image between
rotational display in which the display image is displayed while changing the angle with time, and
nonrotational display in which the angle is not changed.

(Note 2)
The display control unit can
extract center line of the blood vessel,
generate
a first display image in which one-dimensional information, which is obtained by assigning spatial distribution of values of wall shear stress at each position of the blood vessel to each position of the center line, is assigned to the three-dimensional image, and
a second display image in which three-dimensional information, which is obtained by assigning spatial distribution of values of wall shear stress at each position of the blood vessel to each spatial position of the blood vessel, is assigned to the three-dimensional image, and
display the first display image during rotational display of the display image, and display the second display image during nonrotational display of the display image.

(Note 3)
According to at least rotation count or rotation speed of the display image, the display control unit can further change display form of the display image.

(Note 4)
According to magnification or reduction of the display image, the display control unit can further change display form of the display image.

(Note 5)
According to size of display area for displaying the display image, the display control unit can further change display form of the display image.

(Note 6)
During rotational display, the display control unit can vary rotation speed of the display image based on calculation result regarding the wall shear stress.

(Note 7)
During rotational display, the display control unit can perform control to reduce rotation speed at timings for displaying such positions of the blood vessel at which maximum value of the wall shear stress and minimum value of the wall shear stress are calculated.

(Note 8)
During rotational display, the display control unit can perform control to increase rotation speed at timing for displaying such a position of the blood vessel at which calculation result regarding the wall shear stress is incorrect.

(Note 9)
During rotational display, the display control unit can vary rotation speed of the display image based on characteristics of the blood vessel.

(Note 10)
During rotational display, the display control unit can perform control to reduce rotation speed at timing for displaying a position of a lesion area in the blood vessel.

(Note 11)
A determining unit is further included that determines validness of calculation target regarding calculation of the wall shear stress, wherein
the display control unit can display determination result of the validness.

(Note 12)
A determining unit is further included that determines validness of calculation result regarding calculation of the wall shear stress, wherein
the display control unit can display determination result of the validness of the calculation result.

(Note 13)
The display control unit can
display a list in which calculation result regarding the wall shear stress is listed for each subject, and
highlight, in the list, result that is deviating from reference value.

(Note 14)
The display control unit can further display, in the list, analysis result of factors other than the wall shear stress.

(Note 15)
In a display image formed by reflecting value of wall shear stress at each position of a blood vessel in a three-dimensional image of the blood vessel, the display control unit can add, at a position having low validness regarding the calculation result, information indicating the validness and then can display the display image.

(Note 16)
A calculating unit can be further included that calculates values of wall shear stress at each position of the blood vessel; and
a control unit can be further included that transfers calculation result regarding the wall shear stress to a predetermined destination.

(Note 17)
The control unit can transfer calculation result regarding the wall shear stress to a medical report.

(Note 18)
The control unit can transfer information regarding calculation of the wall shear stress to a three-dimensional printer.

(Note 19)
The control unit can transfer calculation result regarding the wall shear stress to a medical image diagnosis apparatus.

(Note 20)
The control unit can change destination for calculation result regarding the wall shear stress according to index value related to blood flow in the blood vessel.

(Note 21)

A control unit can be further included that, based on calculation result regarding the wall shear stress, makes a reservation for an examination apparatus or outputs a notification for prompting a reservation for the examination apparatus.

(Note 22)

A control unit can be further included that, according to a reservation made for collection of medical image data to be used in calculation of the wall shear stress, performs control to secure calculation resource to be used in calculation of the wall shear stress.

(Note 23)

The display control unit can display a display image formed by assigning the values of the wall shear stress to a cross-sectional image indicating a cross-sectional surface of the blood vessel, the input operation receiving unit can receive an input operation for changing position of the cross-sectional surface that is displayed as the display image, and based on calculation result regarding the wall shear stress, the display control unit can vary changing speed of position of the cross-sectional surface according to the input operation.

(Note 24)

The display control unit can display a display image formed by assigning the values of the wall shear stress to a cross-sectional image indicating a cross-sectional surface of the blood vessel, the input operation receiving unit can receive an input operation for changing position of the cross-sectional surface that is displayed as the display image, and the display control unit can vary display form of the display image according to changing speed of position of the cross-sectional surface based on the input operation.

(Note 25)

A medical image processing system including:

a medical image processing apparatus; and a medical image display apparatus, wherein the medical image processing apparatus obtains a three-dimensional image of a blood vessel of a subject and obtains spatial distribution of values of wall shear stress at each position of the blood vessel, and the medical image display apparatus displays, from an arbitrary angle, a display image formed by assigning the values of the wall shear stress to the three-dimensional image, receives an input operation for changing the angle, and during display of the display image formed by assigning the values of the wall shear stress to the three-dimensional image, changes display form of the display image between rotational display in which the display image is displayed while changing the angle with time, and nonrotational display in which the angle is not changed.

(Note 26)

A medical image processing method including:

obtaining that includes obtaining a three-dimensional image of a blood vessel of a subject and obtaining spatial distribution of values of wall shear stress at each position of the blood vessel;

displaying, from an arbitrary angle, a display image formed by assigning the values of the wall shear stress to the three-dimensional image;

receiving an input operation for changing the angle; and changing that, during display of the display image formed by assigning the values of the wall shear stress to the three-dimensional image, includes changing display form of the display image between rotational display in which the display image is displayed while changing the angle with time, and nonrotational display in which the angle is not changed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:

processing circuitry configured to obtain a three-dimensional image of a blood vessel of a subject and obtains spatial distribution of values of wall shear stress at each position of the blood vessel, and display, from an arbitrary angle, a display image formed by assigning the values of the wall shear stress to the three-dimensional image; and an input interface configured to receive an input operation for changing the angle, wherein during display of the display image formed by assigning the values of the wall shear stress to the three-dimensional image, the processing circuitry is configured to change display form of the display image between rotational display in which the display image is displayed while changing the angle with time, and nonrotational display in which the angle is not changed.

2. The medical image processing apparatus according to claim 1, wherein the processing circuitry is configured to extract center line of the blood vessel, generate a first display image in which one-dimensional information, which is obtained by assigning spatial distribution of values of wall shear stress at each position of the blood vessel to each position of the center line, is assigned to the three-dimensional image, and a second display image in which three-dimensional information, which is obtained by assigning spatial distribution of values of wall shear stress at each position of the blood vessel to each spatial position of the blood vessel, is assigned to the three-dimensional image, and display the first display image during rotational display of the display image, and displays the second display image during nonrotational display of the display image.

3. The medical image processing apparatus according to claim 1, wherein, according to at least rotation count or rotation speed of the display image, the processing circuitry further changes display form of the display image.

4. The medical image processing apparatus according to claim 1, wherein, according to magnification or reduction of the display image, the processing circuitry is further configured to change display form of the display image.

5. The medical image processing apparatus according to claim 1, wherein, according to size of display area for displaying the display image, the processing circuitry is further configured to change display form of the display image.

6. The medical image processing apparatus according to claim 1, wherein, during rotational display, the processing circuitry is configured to vary rotation speed of the display image based on calculation result regarding the wall shear stress.

7. The medical image processing apparatus according to claim 6, wherein, during rotational display, the processing circuitry is configured to perform control to reduce rotation speed at timings for displaying such positions of the blood vessel at which maximum value of the wall shear stress and minimum value of the wall shear stress are calculated.

8. The medical image processing apparatus according to claim 6, wherein, during rotational display, the processing circuitry is configured to perform control to increase rotation speed at timing for displaying such a position of the blood vessel at which calculation result regarding the wall shear stress is incorrect.

9. The medical image processing apparatus according to claim 1, wherein, during rotational display, the processing circuitry is configured to vary rotation speed of the display image based on characteristics of the blood vessel.

10. The medical image processing apparatus according to claim 9, wherein, during rotational display, the processing circuitry is configured to perform control to reduce rotation speed at timing for displaying a position of a lesion area in the blood vessel.

11. The medical image processing apparatus according to claim 1, wherein the processing circuitry is configured to
determine validness of calculation target regarding calculation of the wall shear stress, and
display determination result of the validness.

12. The medical image processing apparatus according to claim 1, wherein the processing circuitry is configured to
determine validness of calculation result regarding calculation of the wall shear stress, and
display determination result of the validness of the calculation result.

13. The medical image processing apparatus according to claim 1, wherein the processing circuitry is configured to
display a list in which calculation result regarding the wall shear stress is listed for each subject, and
highlight, in the list, result that is deviating from reference value.

14. The medical image processing apparatus according to claim 13, wherein the processing circuitry is configured to further display, in the list, analysis result of factors other than the wall shear stress.

15. The medical image processing apparatus according to claim 12, wherein, in a display image formed by reflecting value of wall shear stress at each position of a blood vessel in a three-dimensional image of the blood vessel, the processing circuitry is configured to add, at a position having low validness regarding the calculation result, information indicating the validness and then display the display image.

16. The medical image processing apparatus according to claim 1, wherein the processing circuitry is configured to
calculate values of wall shear stress at each position of the blood vessel, and
transfer calculation result regarding the wall shear stress to a predetermined destination.

17. The medical image processing apparatus according to claim 16, wherein the processing circuitry is configured to transfer calculation result regarding the wall shear stress to a medical report.

18. The medical image processing apparatus according to claim 16, wherein the processing circuitry is configured to transfer information regarding calculation of the wall shear stress to a three-dimensional printer.

19. The medical image processing apparatus according to claim 16, wherein the processing circuitry is configured to transfer calculation result regarding the wall shear stress to a medical image diagnosis apparatus.

20. The medical image processing apparatus according to claim 16, wherein the processing circuitry is configured to change destination for calculation result regarding the wall shear stress according to index value related to blood flow in the blood vessel.

21. The medical image processing apparatus according to claim 1, wherein, based on calculation result regarding the wall shear stress, the processing circuitry is configured to make a reservation for an examination apparatus or output a notification for prompting a reservation for the examination apparatus.

22. The medical image processing apparatus according to claim 1, wherein, according to a reservation made for collection of medical image data to be used in calculation of the wall shear stress, the processing circuitry is configured to perform control to secure calculation resource to be used in calculation of the wall shear stress.

23. The medical image processing apparatus according to claim 1, wherein
the processing circuitry is configured to display a display image formed by assigning the values of the wall shear stress to a cross-sectional image indicating a cross-sectional surface of the blood vessel,
the input interface is configured to receive an input operation for changing position of the cross-sectional surface that is displayed as the display image, and
based on calculation result regarding the wall shear stress, the processing circuitry is configured to vary changing speed of position of the cross-sectional surface according to the input operation.

24. The medical image processing apparatus according to claim 1, wherein
the processing circuitry is configured to display a display image formed by assigning the values of the wall shear stress to a cross-sectional image indicating a cross-sectional surface of the blood vessel,
the input interface is configured to receive an input operation for changing position of the cross-sectional surface that is displayed as the display image, and
the processing circuitry is configured to vary display form of the display image according to changing speed of position of the cross-sectional surface based on the input operation.

25. A medical image processing system comprising:
a medical image processing apparatus; and
a medical image display apparatus, wherein
the medical image processing apparatus obtains a three-dimensional image of a blood vessel of a subject and obtains spatial distribution of values of wall shear stress at each position of the blood vessel, and
the medical image display apparatus
displays, from an arbitrary angle, a display image formed by assigning the values of the wall shear stress to the three-dimensional image,
receives an input operation for changing the angle, and
during display of the display image formed by assigning the values of the wall shear stress to the three-dimensional image, changes display form of the display image between rotational display in which the display image is displayed while changing the angle with time, and nonrotational display in which the angle is not changed.

26. A medical image processing method comprising:
obtaining that includes obtaining a three-dimensional image of a blood vessel of a subject and obtaining spatial distribution of values of wall shear stress at each position of the blood vessel;
displaying, from an arbitrary angle, a display image formed by assigning the values of the wall shear stress to the three-dimensional image;
receiving an input operation for changing the angle; and
changing that, during display of the display image formed by assigning the values of the wall shear stress to the three-dimensional image, includes changing display form of the display image between
rotational display in which the display image is displayed while changing the angle with time, and
nonrotational display in which the angle is not changed.

* * * * *